US010968308B2

(12) United States Patent
Chun et al.

(10) Patent No.: US 10,968,308 B2
(45) Date of Patent: Apr. 6, 2021

(54) PREPARATION METHOD OF EPOXY COMPOUND HAVING ALKOXYSILYL GROUP, EPOXY COMPOUND HAVING ALKOXYSILYL GROUP, COMPOSITION COMPRISING THE SAME, AND USE THEREOF

(71) Applicant: KOREA INSTITUTE OF INDUSTRIAL TECHNOLOGY, Cheonan-si (KR)

(72) Inventors: Hyun Aee Chun, Suwon-si (KR); Yun Ju Kim, Ansan-si (KR); Sook Yeon Park, Gunpo-si (KR); Su Jin Park, Osan-si (KR)

(73) Assignee: KOREA INSTITUTE OF INDUSTRIAL TECHNOLOGY, Choongcheongnam-do (KR)

( * ) Notice: Subject to any disclaimer, the term of this patent is extended or adjusted under 35 U.S.C. 154(b) by 39 days.

(21) Appl. No.: 16/181,351

(22) Filed: Nov. 6, 2018

(65) Prior Publication Data

US 2019/0135970 A1 May 9, 2019

(30) Foreign Application Priority Data

Nov. 7, 2017 (KR) .......................... 10-2017-0147526

(51) Int. Cl.
*C07C 29/10* (2006.01)
*C07C 269/02* (2006.01)
(Continued)

(52) U.S. Cl.
CPC ............ *C08G 18/58* (2013.01); *C07C 29/106* (2013.01); *C07C 269/02* (2013.01);
(Continued)

(58) Field of Classification Search
None
See application file for complete search history.

(56) References Cited

U.S. PATENT DOCUMENTS 9,150,686 B2    10/2015    Chun et al.
9,725,590 B2    8/2017    Chun et al.
(Continued)

FOREIGN PATENT DOCUMENTS

EP    2826777 A1    1/2015
EP    2960245 A1    12/2015
(Continued)

OTHER PUBLICATIONS

Japanese Office Action for JP Application No. 2018-209795 dated Sep. 18, 2019, citing the above references.
The Extended European Search Report for corresponding EP Application No. 18204761.3 dated Apr. 10, 2019, citing the above references.

*Primary Examiner* — Richard A Huhn
(74) *Attorney, Agent, or Firm* — Cantor Colburn LLP

(57) ABSTRACT

Provided are a preparation method of an epoxy compound having an alkoxysilyl group in which an increase in the epoxy equivalent weight (EEW) of the epoxy compound is minimized because alkoxysilylation occurs through a simple one-step reaction using a hydroxyl group formed during the synthesis of the epoxy compound, an epoxy compound having an alkoxysilyl group prepared by the method, a composition comprising the same, and a use thereof. The method includes the reaction of an epoxy compound having a hydroxyl group with an isocyanate alkoxysilane in the presence of amine-based base catalyst, wherein the epoxy compound having an alkoxysilyl group has a mole ratio of [epoxide group]:[alkoxysilyl group] of n:1 ranging from 2:1 to 10:1, and an EEW increase of the epoxy compound having an alkoxysilyl group is less than 260/n. The epoxy compound has good physical properties when being cured.

6 Claims, 2 Drawing Sheets

(51) Int. Cl.
*C07D 303/48* (2006.01)
*C07D 407/14* (2006.01)
*C08G 18/58* (2006.01)
*C07F 7/18* (2006.01)
*C08G 18/18* (2006.01)
*C08G 59/14* (2006.01)
*C09J 163/00* (2006.01)
*C08G 59/32* (2006.01)
*C08G 18/20* (2006.01)
*C08G 18/71* (2006.01)

(52) U.S. Cl.
CPC .......... *C07D 407/14* (2013.01); *C07F 7/1804* (2013.01); *C08G 18/18* (2013.01); *C08G 18/1808* (2013.01); *C08G 18/2018* (2013.01); *C08G 18/2027* (2013.01); *C08G 18/581* (2013.01); *C08G 18/718* (2013.01); *C08G 59/1433* (2013.01); *C08G 59/1477* (2013.01); *C08G 59/3281* (2013.01); *C09J 163/00* (2013.01); *C07F 7/1892* (2013.01)

(56) References Cited

U.S. PATENT DOCUMENTS

| | | |
|---|---|---|
| 2008/0214734 A1 | 9/2008 | Yang et al. |
| 2015/0105493 A1 | 4/2015 | Chun et al. |
| 2015/0203626 A1 | 7/2015 | Chun et al. |
| 2015/0361211 A1* | 12/2015 | Chun .................. C09D 163/00 428/76 |

FOREIGN PATENT DOCUMENTS

| | | |
|---|---|---|
| JP | 5297598 B2 | 9/2013 |
| JP | 2017181890 A | 10/2017 |
| KR | 101252063 B1 | 4/2013 |
| KR | 1020130111299 A | 10/2013 |
| KR | 1020140009029 A | 1/2014 |
| KR | 1020140106441 A | 9/2014 |
| KR | 1020150105213 A | 9/2015 |
| KR | 101596880 B1 | 2/2016 |

* cited by examiner

PREPARATION METHOD OF EPOXY COMPOUND HAVING ALKOXYSILYL GROUP, EPOXY COMPOUND HAVING ALKOXYSILYL GROUP, COMPOSITION COMPRISING THE SAME, AND USE THEREOF

CROSS-REFERENCE TO RELATED APPLICATION(S)

This application claims benefit of priority to Korean Patent Application No. 10-2017-0147526 filed on Nov. 7, 2017 in the Korean Intellectual Property Office, the disclosure of which is incorporated herein by reference in its entirety.

BACKGROUND

1. Field

The present disclosure relates to a new preparation method of epoxy compound having an alkoxysilyl group, using a hydroxyl group formed, during the synthesis of epoxy compound, an epoxy compound having an alkoxysilyl group prepared by the method, a composition comprising the same, and use thereof. More specifically, the present disclosure relates to a new preparation method of an epoxy compound having an alkoxysilyl group in which an increase in the epoxy equivalent weight (EEW) of the epoxy compound associated with the alkoxysilylation is minimized through a simple one-step reaction, an epoxy compound having an alkoxysilyl group prepared by the method, a composition comprising the same, and a use thereof.

2. Description of Related Art

Epoxy compounds (resins) have good mechanical property, electrical insulation, heat resistance, water resistance, adhesive characteristics, and the like, and have been thus widely used in applications such as paintings, printed circuit boards, integrated circuit (IC) encapsulants, electric and electronic components, and adhesives.

Although research has been constantly undertaken in order to decrease the coefficient of thermal expansion (CTE) of epoxy compounds (resins), the CTE of epoxy is still higher than required levels. For example, epoxy resins (epoxy compounds) used in semiconductor packaging significantly limit the reliability and processability of the semiconductor packaging because the CTE of the epoxy resin is higher than that of silicon. Therefore, the development of epoxy systems having improved thermal expansion characteristics is required.

In general, epoxy resins (epoxy compounds) are prepared through a reaction of epichlorohydrin with a multifunctional hydroxylic compound in the presence of a base catalyst. That is, first, 1,2-chlorohydrin is formed via the reaction of the epoxide group of epichlorohydrin with a hydroxylic compound in the presence of a base catalyst, and then an epoxy resin is prepared from a ring closing reaction through dehydrochlorination. However, in such preparation conditions of epoxy resin, side reactions occur, such as the formations of 1,2-chlorohydrin, which does not proceed to be ring-closure, 1,3-chlorohydrin due to β-addition, and 1,2-glycol produced by hydrolysis of produced epoxy rings and oligomers formed from the reaction of the epoxide with the hydroxylic compound of a starting material. Therefore, most commercial epoxy resins-consist of a mixture of an epoxy resin having only an epoxide functional group and an epoxy resin having an epoxide group and a hydroxyl group formed due to the side reaction. Reaction Formula 1 below schematically illustrates an epoxy resin having a hydroxyl group formed by side reaction, and such an epoxy resin has two or more epoxide groups.

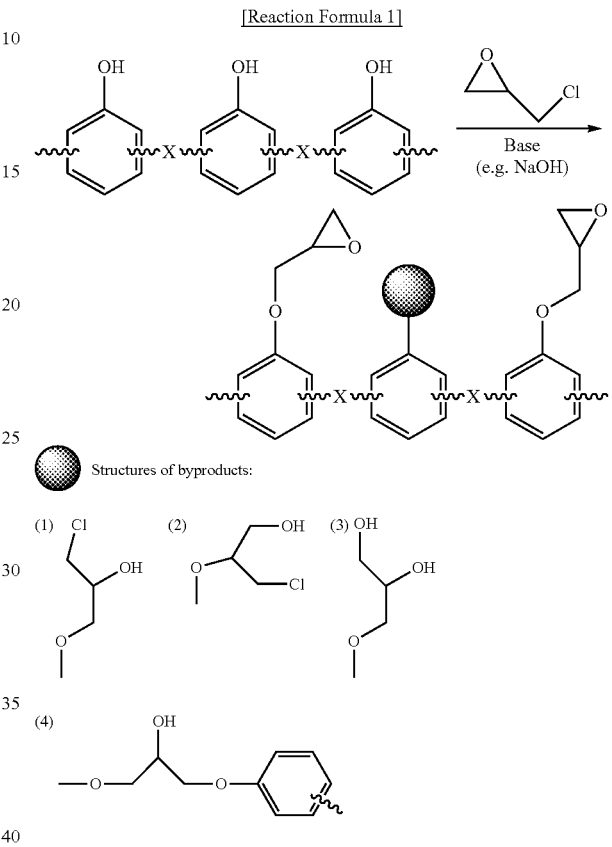

[Reaction Formula 1]

(The structure of the epoxy compound (epoxy resin) having a hydroxyl group is simply illustrated to help understanding. Functional groups having hydroxyl groups formed by side reaction are diverse, as shown in the above formulae (1) to (4), and diverse combinations of such functional groups may exist in an oligomer having a plurality of repeating units. This will be obvious to those of ordinary skill in the art and thus will not be described in detail.)

However, if an epoxy resin has a hydroxyl group (which can not be converted into an epoxy ring), it results in the increase of the epoxy equivalent weight (EEW) of the epoxy resin. In addition, since the hydroxyl group does not participate in an epoxy curing reaction, it deteriorates physical properties of a cured epoxy system.

The applicant of the present application has developed the new epoxy compounds having alkoxysilyl groups (Korean Patent Application Nos. 10-2012-0093320, 10-2013-0027308, 10-2013-0078347, 10-2013-0111473, 10-2014-0021884, etc.), and observed that when an alkoxysilyl group was introduced to an epoxy compound, the heat resistance of an epoxy composite comprising the epoxy compound, markedly increased when the epoxy composite was prepared.

In Korean Patent Application Nos. 10-2013-0027308 and 10-2013-0078347, an epoxy compound having a hydroxyl group is synthesized by the partial epoxidation of an aromatic alcohol of a starting material hereinafter, referred to as an "epoxy resin intermediate having a hydroxyl group", and an epoxy compound having an alkoxysilyl group is prepared by reacting a residual hydroxyl group with an isocyanate alkoxysilane. However, when the "epoxy compound intermediate having a hydroxyl group" is synthesized using this method, it has difficulty in controlling the structure of the intermediate. For example, when the amount of epichlorohydrin used is decreased in order to leave the unreacted OH groups, the remaining aromatic OH groups react with the epoxide groups, which result in the increase of the molecular weight of epoxy and consequently an increase in EEW (Epoxy Equivalent Weight, calculated by dividing the total molecular weight of an epoxy resin (epoxy compound) by the number of epoxide functional groups). However, if a excess amount of epichlorohydrin is added to solve this problem, all OH groups may participate in a reaction, and thus it may be difficult to prepare the "epoxy resin intermediate having a hydroxyl group."

According to preparation method of alkoxysilylated epoxy compounds disclosed in Korean Patent Application Nos. 10-2013-0111473 and 10-2014-0021884, an epoxy compound having an alkoxysilyl group is prepared by a ring opening of an epoxide group of an epoxy compound and alkoxysilyl group is introduced to a secondary OH group formed by the ring opening. Reactions for the preparation of alkoxysilylated epoxy compounds using an ortho-cresol novolac epoxy compound according to the above-identified Korean applications are schematically shown in FIG. 1.

As shown in FIG. 1, in the epoxy compound having an alkoxysilyl group prepared by the methods in the patent applications, (1) the epoxide group of the epoxy resin is consumed due to an epoxy ring-opening reaction, and (2) a reactant (ring-opening agent) is incorporated to the structure of the epoxy compound, consequently the EEW of the alkoxysilylated epoxy resin obtained finally is increased. Such an increase in the EEW of the epoxy compound has an effect on the curing rate and crosslinking density of the epoxy compound. For example, if an alkoxysilylated epoxy compound having a mole ratio of [epoxide group]:[alkoxysilyl group] of 4:1 is synthesized by a ring-opening method using an epoxy compound having an EEW of 200 g/Eq, an epoxy compound having an EEW>324 g/Eq is obtained. If the ratio of silylation increases to 2:1, the alkoxysilylated epoxy compound thus obtained has an EEW>450 g/Eq, which is about 130% or higher than the EEW of the initial epoxy compound. Moreover, it is inconvenient to remove a strong base (for example, NaOH) used in a first step of ring opening completely to suppress side reactions in a second step of alkoxysilylation.

Therefore, there is a need for a new preparation method of an epoxy compound having an alkoxysilyl group, which is simple compared to methods of related art, minimizes an EEW increase of epoxy compounds due to the alkoxysilylation and solves the problems of the related art.

In addition, there is a need for a preparation method of an epoxy compound having an alkoxysilyl group which minimizes the an EEW increase and exhibits good curing characteristics upon curing, and there is a need for an epoxy compound having an alkoxysilyl group with such characteristics.

Therefore, the present disclosure provides a preparation method of an epoxy compound having an alkoxysilyl group using a hydroxyl group formed during the preparation of the epoxy compound, and an epoxy compound having an alkoxysilyl group prepared by the method with the good heat resistance in an epoxy composite, that is, low CTE characteristics. That is, the epoxy compound having an alkoxysilyl group is synthesized by reacting a hydroxyl group of an epoxy compound (formed since an epoxy ring closing reaction does not proceed) with a silane coupling agent to convert the hydroxyl group to a reactive alkoxysilyl group. Furthermore, an increase in the EEW of the epoxy compound having an alkoxysilyl group is minimized.

SUMMARY

An aspect of the present disclosure may include a preparation method of an epoxy compound having an alkoxysilyl group by converting a hydroxyl group formed during the synthesis of the epoxy compound to an alkoxysilyl group which (1) contributes to an interfacial reaction with an inorganic substance and (2) participates in an epoxy curing reaction.

An aspect of the present disclosure may also provide a preparation method of an epoxy compound having an alkoxysilyl group through a simple one-step reaction, which is able to minimize an EEW increase of the epoxy compound.

An aspect of the present disclosure may also provide an epoxy compound having an alkoxysilyl group capable of minimizing an EEW increase thereof and having good curing characteristics.

An aspect of the present disclosure may also provide a composition, an electronic material, and a cured product comprising the epoxy compound of the present disclosure.

According to a first aspect of the present disclosure, a preparation method of an epoxy compound having an alkoxysilyl group may include reacting an epoxy compound having a hydroxyl group with an isocyanate alkoxysilane of Formula 1 below in the presence of at least one amine-based base catalyst selected from the group consisting of triethylamine, diisopropylethylamine, pyridine, and imidazole, wherein the epoxy compound having an alkoxysilyl group has a mole ratio of [epoxide group]:[alkoxysilyl group], n:1 ranging from 2:1 to 10:1, and an EEW increase of the epoxy compound having an alkoxysilyl group may be less than 260/n (where n is mole ratio of an epoxide group to 1 mol of the alkoxysilyl group in the epoxy compound having an alkoxysilyl group, and n ranges from 2 to 10) compared to an EEW of the epoxy compound having a hydroxyl group, $$OCN(CH_2)_3SiR_1R_2R_3 \qquad \text{[Formula 1]}$$

where at least one of $R_1$ to $R_3$ is an alkoxy group having 1 to 5 carbon atoms, and the remainder are alkyl groups having 1 to 10 carbon atoms.

According to a second aspect of the present disclosure, in the method of the first aspect, the epoxy compound having a hydroxyl group may be at least one selected from the group consisting of Formulae AS to IS below:

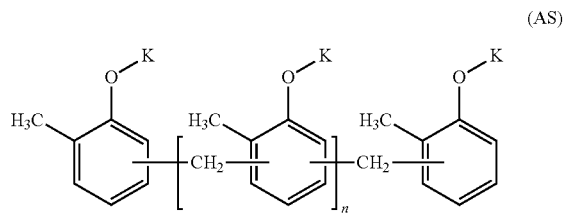

(AS)

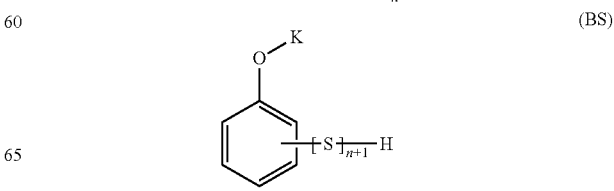

(BS)

-continued
(CS)
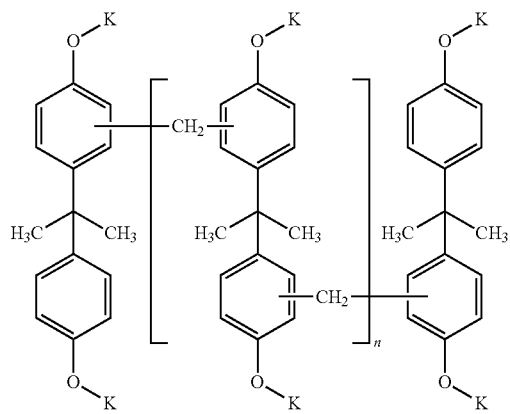
(DS)
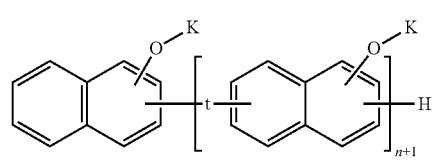
(ES)
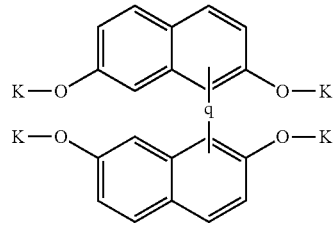
(FS)
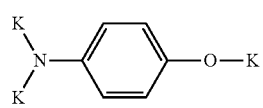
(GS)
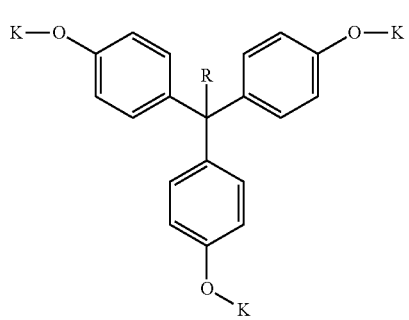
(HS)
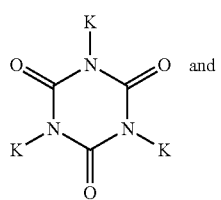
and
(IS)
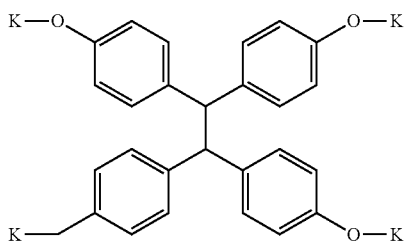
in Formula BS, S is
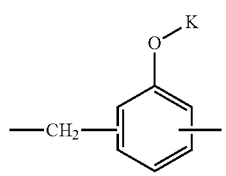
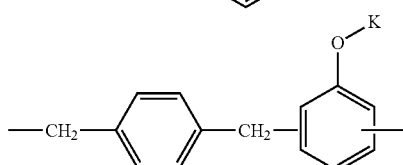
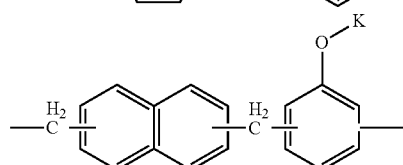
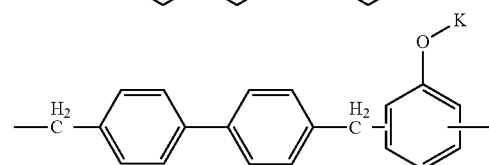
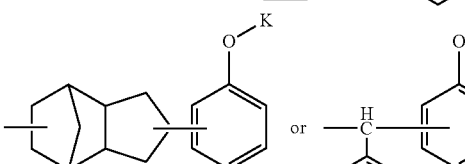
or 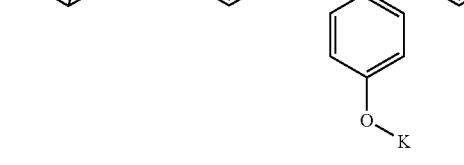,
in Formula DS, t is
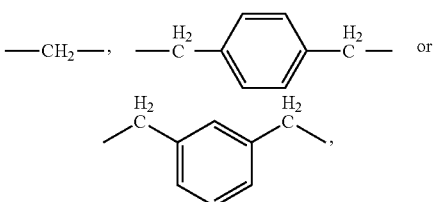
or 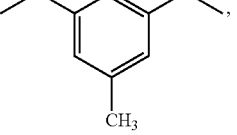, in Formulae AS to DS, n is an integer equal to or greater than 1, in Formula ES, -q- is —CH$_2$— or a direct linkage, in Formula GS, R is hydrogen, a hydroxyl group, a C1-C10 alkyl group, or a C6 or C10 aromatic group, in Formulae AS to IS, at least one of Ks is a structure having a hydroxyl group selected from the group consisting of —CH$_2$CHOHCH$_2$OH (Formula S11), —CH$_2$CHOHCH$_2$Cl (Formula S12), and —CH (CH$_2$OH) (CH$_2$Cl) (Formula S13), and the remainder are structures having an epoxide group of Formula E1 below:

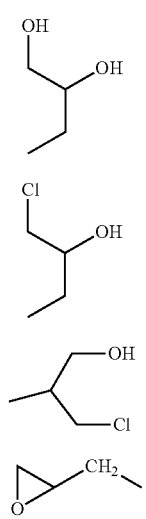

The structures of Formulae AS to IS may be connected through a linker having a hydroxyl group of Formula LG1 below at one position of Ks:

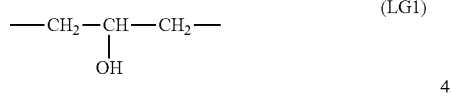

According to a third aspect of the present disclosure, in the method of the first or second aspect, 1 equivalent of the hydroxyl group of the epoxy compound having a hydroxyl group may reacted with 1 equivalent of the isocyanate alkoxysilane of Formula 1. According to a fourth aspect of the present disclosure, in the method of any one of preceding aspects, 0.5 to 1 equivalent of the amine-based base catalyst may be used per 1 equivalent of the hydroxyl group of the epoxy compound having a hydroxyl group. According to a fifth aspect of the present disclosure, in the method of any one of preceding aspects, the reacting may be performed at a temperature range of 90° C. to 150° C. According to a sixth aspect of the present disclosure, in the method of any one of preceding aspects, the reacting may be performed for 72 hours to 120 hours.

According to a seventh aspect of the present disclosure, in the method of any one of preceding aspects, the epoxy compound having an alkoxysilyl group may be at least one selected from the group consisting of Formulae AF to IF below:

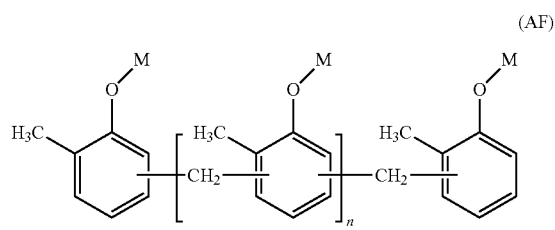

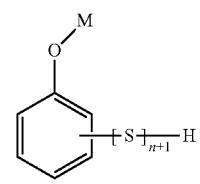

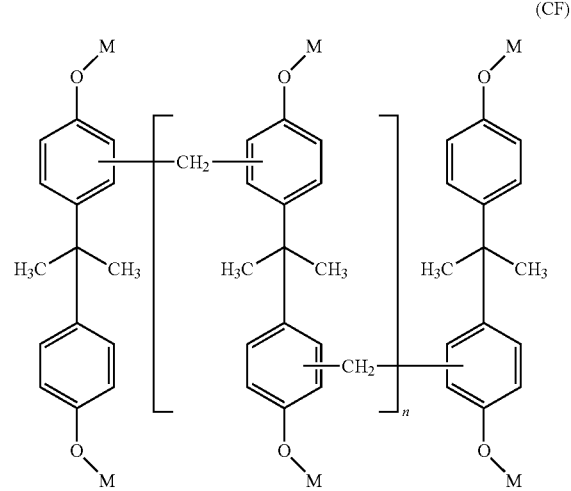

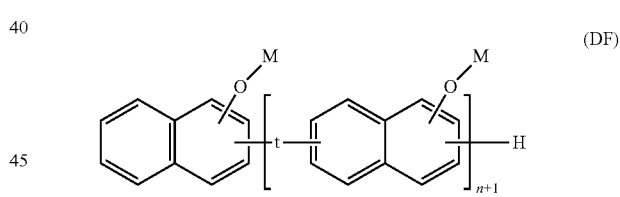

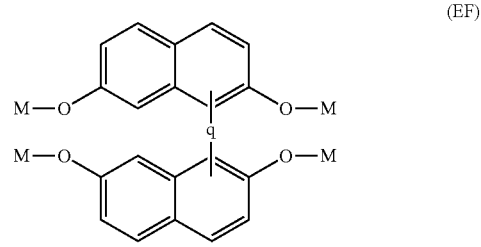

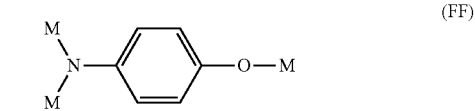

-continued (GF)
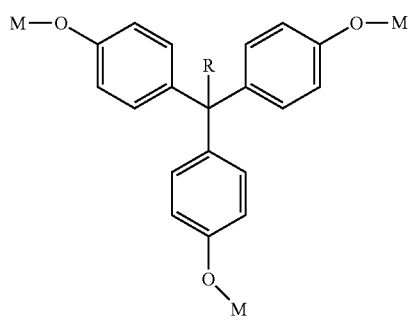

(HF)
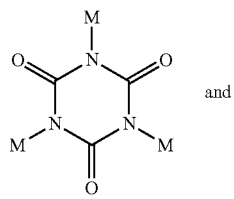
and (IF)
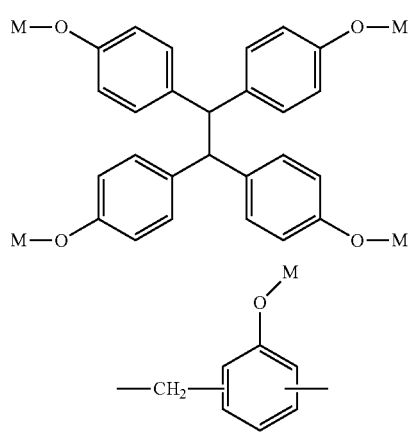

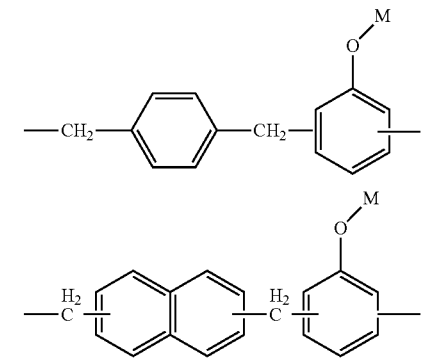

in Formula BF, S is

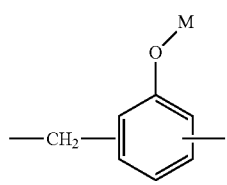

-continued

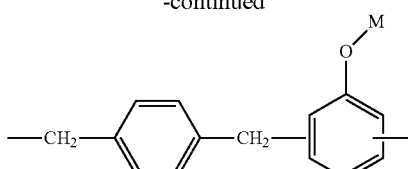

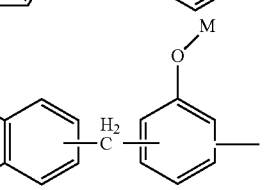

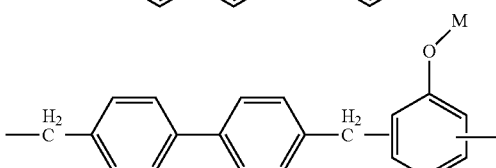

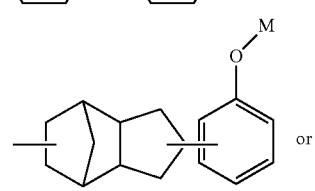

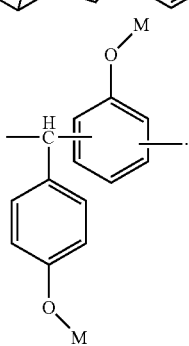

in Formula DF, t is

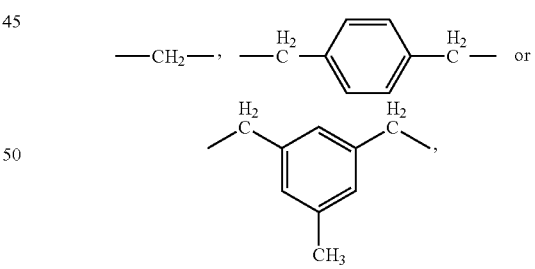

in Formulae AF to DF, n is an integer equal to or greater than 1, in Formula EF, -q- is —CH$_2$— or a direct linkage, in Formula GF, R is hydrogen, a hydroxyl group, a C1-C10 alkyl group, or a C6 or C10 aromatic group, in Formulae AF to IF, at least one of Ms is a structure having an alkoxysilyl group selected from the group consisting of —CH$_2$CHOXCH$_2$OX (Formula S21), —CH$_2$CHOXCH$_2$Cl (Formula S22), and —CH(CH$_2$OX)(CH$_2$Cl) (Formula S23), and the remainder are structures having an epoxide group of Formula E1 below:

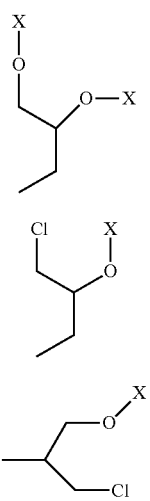

(S21)

(S22)

(S23)

in Formulae S21 to S23, X is $CONH(CH_2)_3SiR_1R_2R_3$, and at least one of $R_1$ to $R_3$ is an alkoxy group having 1 to 5 carbon atoms and the remainder are alkyl groups having 1 to 10 carbon atoms,

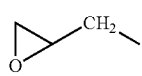

(E1)

The structures of Formulae AF to IF may be connected to each other at one of Ms through a linker having an alkoxysilyl group of Formula LG2 below:

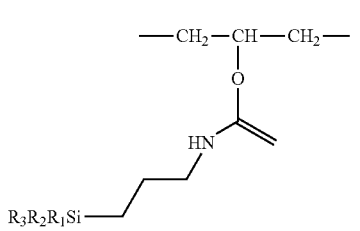

(LG2)

in Formula LG2, at least one of $R_1$ to $R_3$ is an alkoxy group having 1 to 5 carbon atoms, and the remainder are alkyl groups having 1 to 10 carbon atoms.

According to an eighth aspect of the present disclosure, an epoxy compound comprising an alkoxysilyl group, wherein the epoxy compound comprising an alkoxysilyl group has a mole ratio of [epoxide group]:[alkoxysilyl group] of n:1 ranging from 2:1 to 10:1 is provided. According to a ninth aspect of the present disclosure, the epoxy compound comprising an alkoxysilyl group of the eighth aspect may be prepared using an epoxy compound having a hydroxyl group, and an EEW increase of the epoxy compound comprising an alkoxysilyl group may be less than 260/n (where n is a mole ratio of the epoxide group to 1 mol of the alkoxysilyl group in the epoxy compound comprising an alkoxysilyl group, and n ranges from 2 to 10) compared to an EEW of the epoxy compound having a hydroxyl group. According to a tenth aspect of the present disclosure, the epoxy compound comprising an alkoxysilyl group of the eighth or ninth aspect may be represented by Formulae AF to IF defined above.

According to an eleventh aspect of the present disclosure, an epoxy resin composition may comprise the epoxy compound comprising an alkoxysilyl group of any one of the eighth to tenth aspects, a curing agent, and a filler. The epoxy resin composition may comprise at least one epoxy compound having an alkoxysilyl group of the present disclosure.

According to a twelfth aspect of the present disclosure, a cured product may be obtained by curing the composition of the eleventh aspect.

According to a thirteenth aspect of the present disclosure, an electronic material may comprise the composition of the eleventh aspect. According to a fourteenth aspect of the present disclosure, the electronic material of the thirteenth aspect may be selected from the group consisting of a substrate, a film, prepreg, a laminate, a printed circuit board, a semiconductor device, and a packaging material.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION

Figure 1:
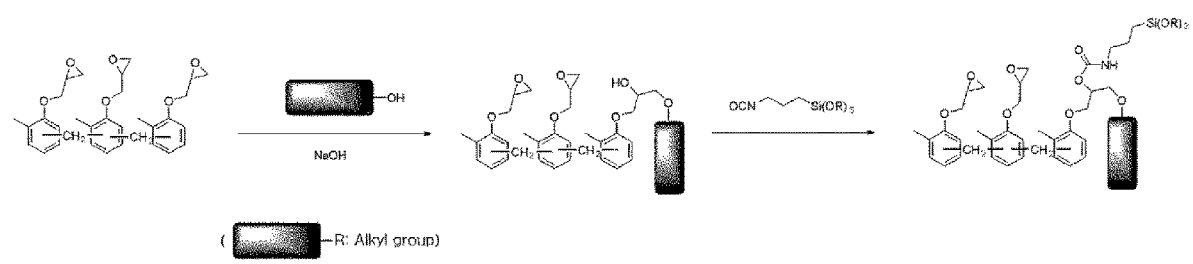
FIG. 1 is a reaction schematic for the preparation of alkoxysilylated epoxy compounds in accordance with the prior art.
Figure 2:
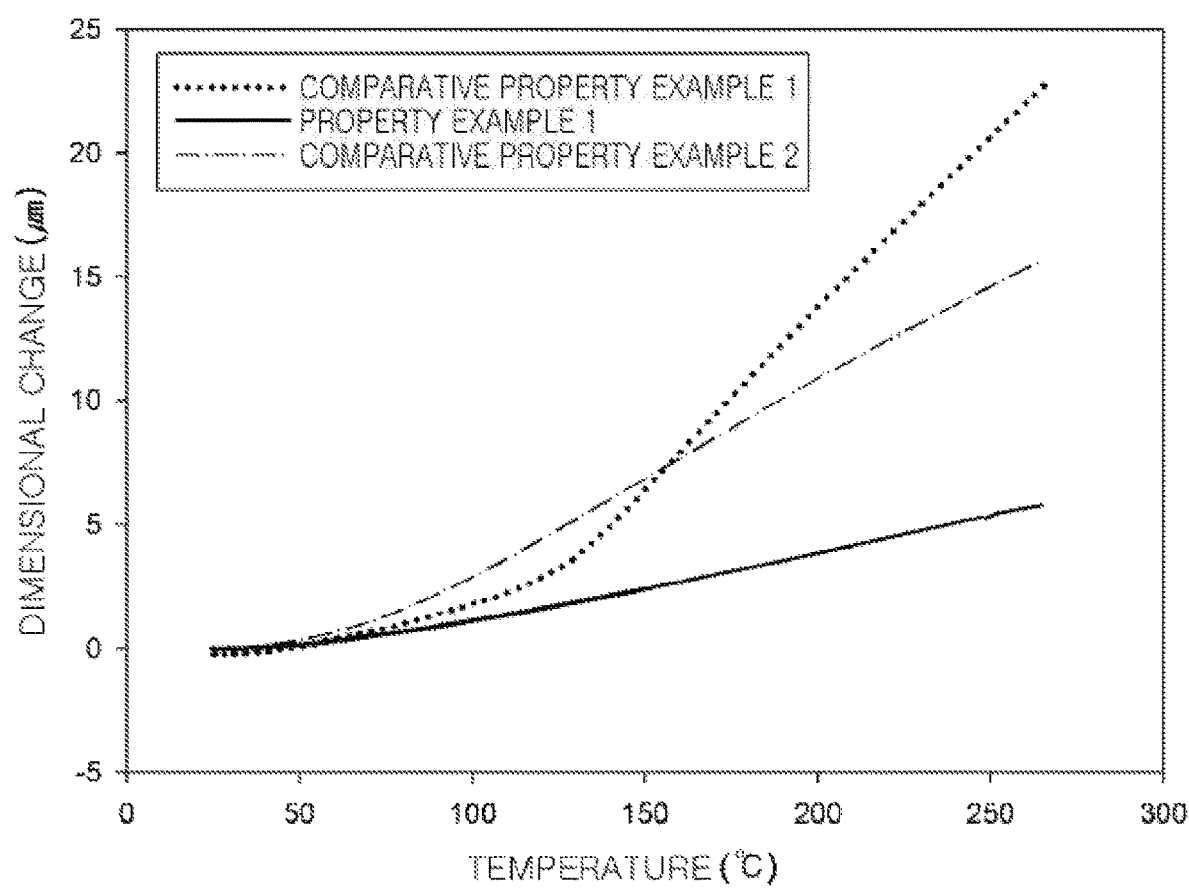
FIG. 2 is a graph illustrating thermal expansion characteristics (dimensional changes as a function of the temperature) of Property Example 1 and Comparative Property Examples 1 and 2.

The present disclosure provides a simple and efficient preparation method of an epoxy compound having an alkoxysilyl group by converting a hydroxyl group existing in an epoxy compound into a reactive alkoxysilyl group. According to the present disclosure, the epoxy compound having an alkoxysilyl group is prepared by a reaction between a hydroxyl group of an epoxy compound and isocyanate alkoxysilane.

As described above, in general, an epoxy compound (epoxy resin) of the related art prepared by a reaction of an active hydrogen compound (for example, a polyphenol) with epichlorohydrin may have a hydroxyl group (OH group) formed by a side reaction, in addition to an epoxide group. In addition, the epoxide group participates in a curing reaction, but the OH group does not participate in the curing reaction. Thus, the OH group may have a negative effect on the physical properties of a cured product of the epoxy resin.

Therefore, in the preparation method of the present disclosure, when the epoxy compound is prepared, the hydroxyl group formed by a side reaction is converted to alkoxysilyl group to prepare an epoxy compound having an alkoxysilyl group. That is, as shown in the mechanisms of Reaction Formulae 3 and 4, in the preparation method of an epoxy compound having an alkoxysilyl group of the present disclosure, a hydroxyl group of the epoxy compound is converted to alkoxysilyl group.

[Reaction Formula 3]
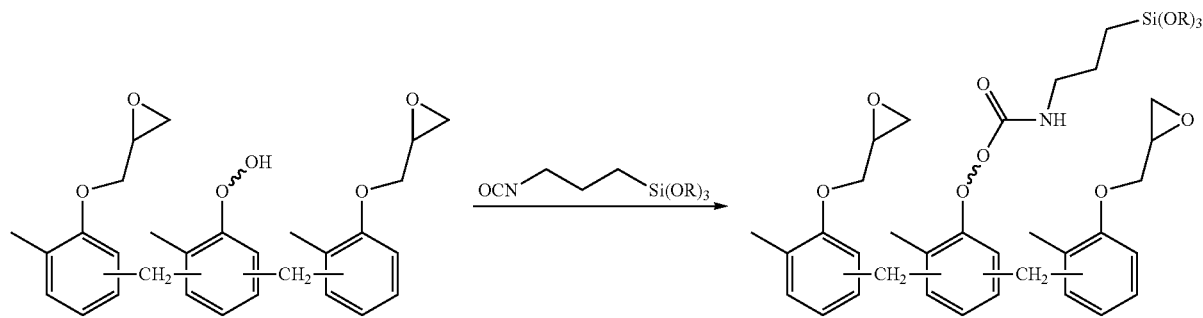
(∼∼∼∼∼ Simply illustrates a structure to which a hydroxyl group is connected)
[Reaction Formula 4]
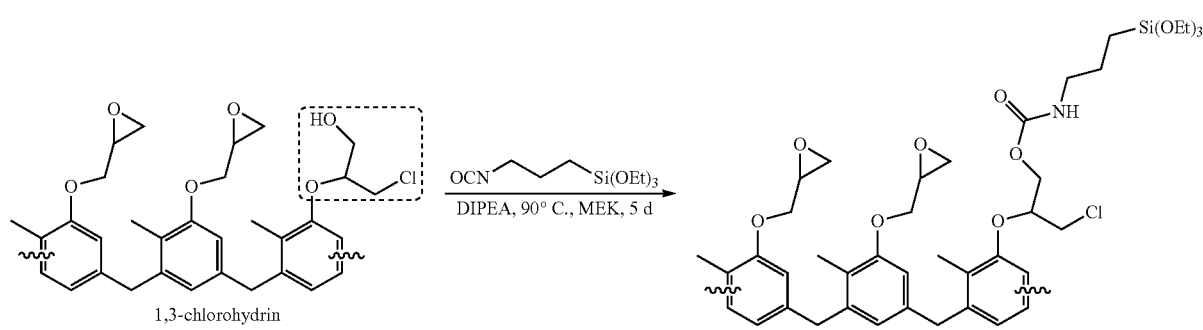
1,3-chlorohydrin
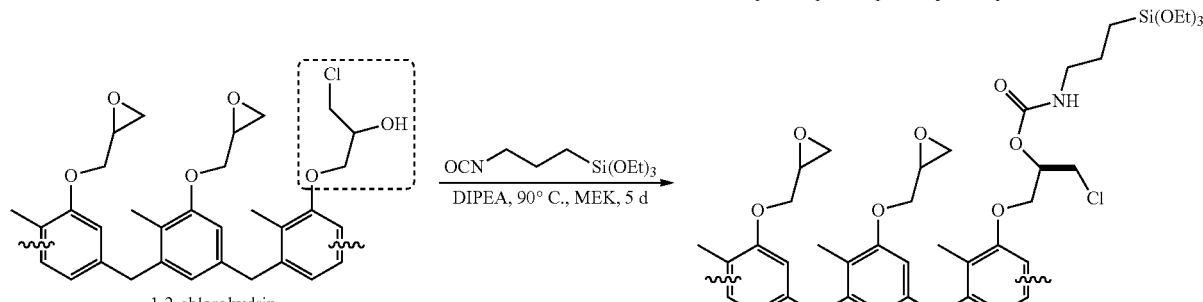
1,2-chlorohydrin
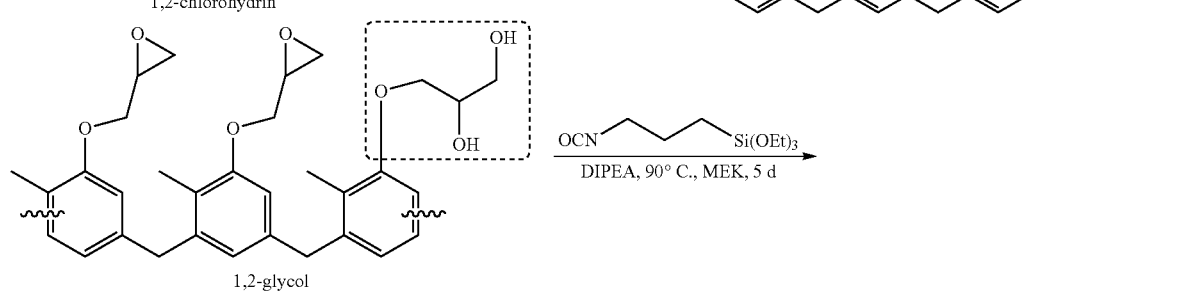
1,2-glycol
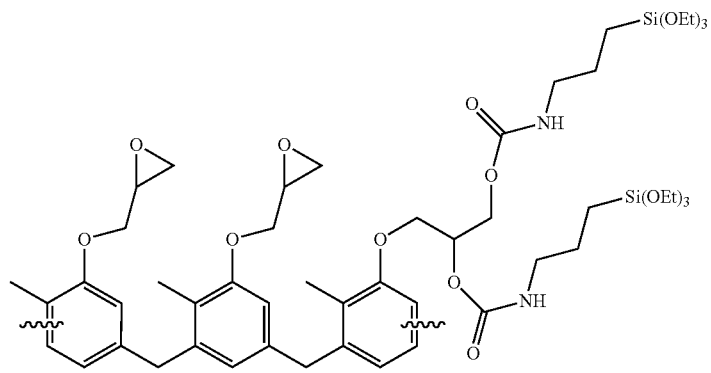

Reaction Formula 3 simply illustrates a mechanism in which a hydroxyl group is converted to alkoxysilyl group in the preparation method of the present disclosure, and Reaction Formula 4 illustrates an example mechanism in which specific structural units having hydroxyl groups of epoxy compounds are converted to alkoxysilyl group. According to the method of the present disclosure, in addition to the structural units having a hydroxyl group, specifically shown in Reaction Formula 4, a structural unit having a hydroxyl group formed in general epoxy compound synthesis may also be converted to alkoxysilyl group.

In the method of the present disclosure, the epoxy compound, specifically, an epoxy resin having an alkoxysilyl group, is prepared by alkoxysilylation of a hydroxyl group through a reaction between an epoxy resin having a hydroxyl group and isocyanate alkoxysilane. Therefore, the present disclosure provides a preparation method of an epoxy compound having an alkoxysilyl group comprising, consisting essentially of, or consisting of by reacting an epoxy compound having a hydroxyl group with isocyanate alkoxysilane in the presence of at least one amine-based base catalyst selected from the group consisting of triethylamine, diisopropylethylamine, pyridine, and imidazole.

In the present specification, the term "epoxy compound" refers to an epoxy compound having at least two epoxide functional groups and includes an epoxy resin generally known in the related technical field.

In the present disclosure, the epoxy compound, specifically, an epoxy resin having a hydroxyl group used for preparing the epoxy compound having an alkoxysilyl group is an epoxy compound having at least one hydroxyl group and at least two epoxide groups.

The epoxy compound having a hydroxyl group may be any epoxy compound having a hydroxyl group as long as the epoxy equivalent weight (EEW) of the epoxy compound is 5% or more higher than the EEW of an epoxy compound synthesized without any side reactions (that is, an epoxy resin having an epoxide group only but not having a hydroxyl group). For example, when an ortho-cresol novolac epoxy compound is synthesized without side reactions, the EEW of an epoxy compound is 176 g/Eq. Being compared, if the ortho-cresol novolac epoxy compound has an EEW of 5% or more higher (that is, >184.8 g/Eq), it may be used to prepare the epoxy compound having an alkoxysilyl group of the present disclosure. Specifically, an epoxy compound having an EEW within the range of 100 g/Eq to 400 g/Eq, preferably within the range of 100 g/Eq to 300 g/Eq, may be used as a reactant in the method of the present disclosure. That is, since the EEW of an epoxy compound is determined by the molecular structure of the epoxy compound, an epoxy compound having a hydroxyl group in the above-mentioned EEW range has some hydroxyl groups per molecules, and thus, an epoxy compound having an alkoxysilyl group may be prepared by alkoxysilylation of the hydroxyl groups.

Furthermore, in general, the side reactions are accompanied as described above when an epoxy compound is prepared, and thus, most commercial epoxy compounds are in the form of a mixture of an epoxy compound having an epoxide group only and an epoxy compound having an epoxide group and a hydroxyl group formed by a side reaction, or in the form of combination of various monomers and/or oligomers in which various repeating units having an epoxide group and/or a hydroxyl group are variously combined. In the preparation method of an alkoxysilyl group of the present disclosure, such a commercial epoxy compound (commercially available epoxy compound), specifically, an epoxy resin, may be used as received. Such a commercial epoxy compound is general technical knowledge to those of ordinary skill in the art, and thus a detailed description thereof will not be provided.

For example, the epoxy compound having a hydroxyl group may include a bisphenol, biphenyl, naphthalene, benzene, isocyanurate, triphenylmethane, 1,1,2,2-tetraphenylethane, tetraphenylmethane, 4,4'-diaminodiphenylmethane, aminophenol, alicyclic, aliphatic, or novolac unit.

Specifically, the epoxy compound having a hydroxy group may be one selected from the group consisting of Formulae AS to IS:

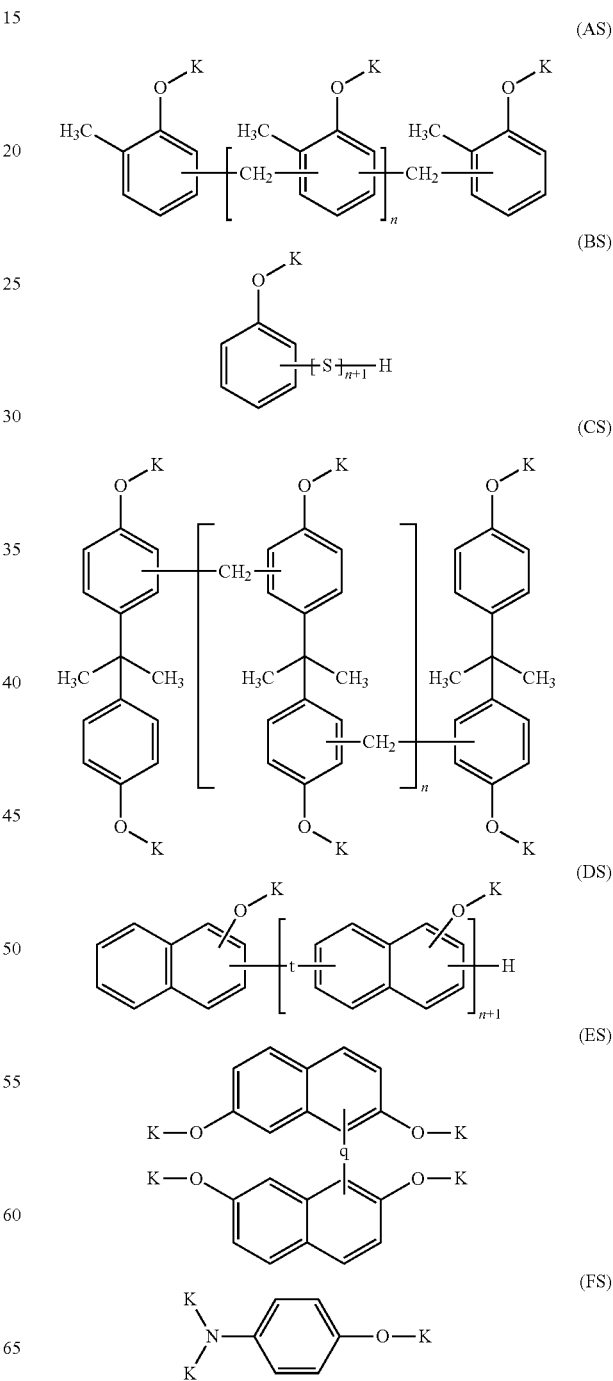

-continued (GS)
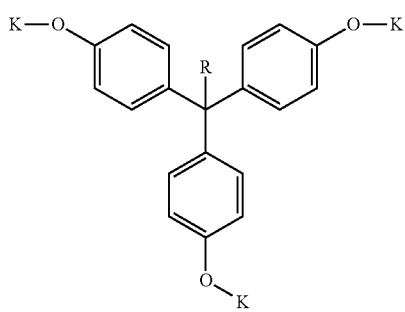

(HS)
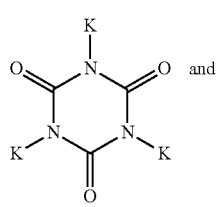 and (IS)
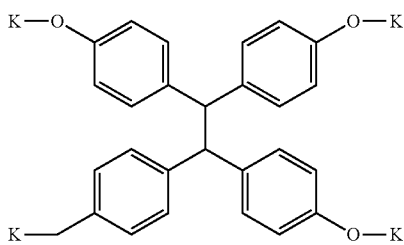

In Formula B, S is

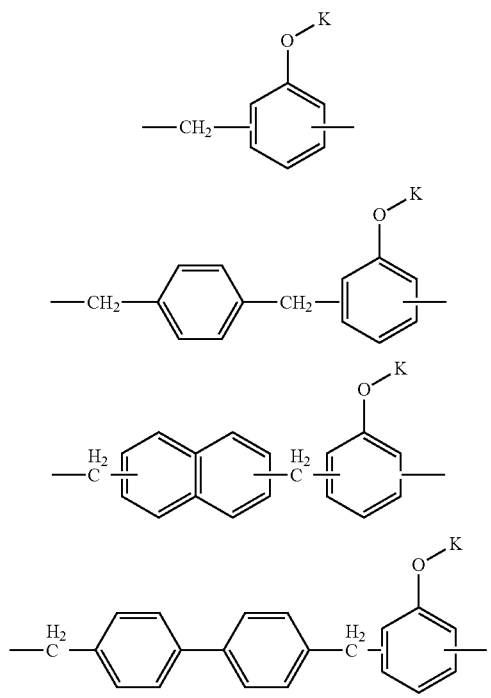

-continued

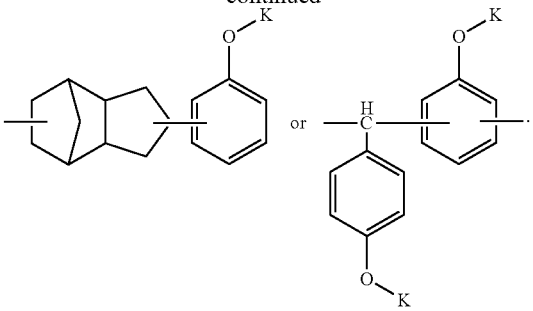

In Formula DS, t is

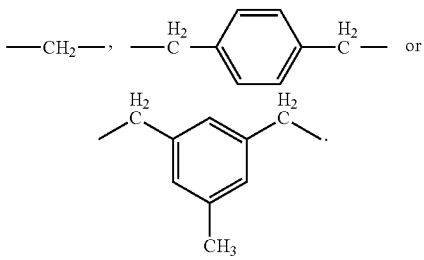

In Formulae AS to DS, n is an integer equal to or greater than 1, preferably an integer ranging from 1 to 30.

In Formula ES, -q- is —CH$_2$— or a direct linkage.

In Formula GS, R is hydrogen, a hydroxyl group, a C1-C10 alkyl group, or a C6 or C10 aromatic group.

In Formulae AS to IS, at least one of Ks is a structure having a hydroxyl group, and the remainder are structures having an epoxide group of Formula E1, preferably, at least two of the remainder are structures having an epoxide group of Formula E1.

The structure having a hydroxyl group is selected from the group consisting of —CH$_2$CHOHCH$_2$OH (Formula S11), —CH$_2$CHOHCH$_2$Cl (Formula S12), and —CH(CH$_2$OH)(CH$_2$Cl) (Formula S13).

(S11)

(S12)

(S13)
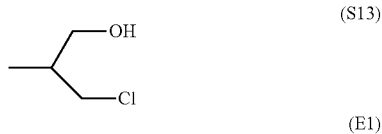

(E1)

The epoxy compound having a hydroxyl group may be any epoxy compound having a hydroxyl group which is a monomer, an oligomer, or a mixture thereof. The term "monomer" refers to one kind of monomer and also a mixture of identical or different monomers. The term "oligomer" refers to an oligomer having a combination or mixture of identical or different repeating units.

At least two structures selected from the group consisting of Formulae AS to IS may be connected to each other, and in this case, the structures may be a polymer connected at any position of Ks via a linker having a hydroxyl group of Formula LG1. The hydroxyl group of the linker of Formula LG1 may also be alkoxysilylated. For example, when two structures of Formula AS are connected to each other, one of Ks of one of the structures of Formula AS is connected to one of Ks of the other of the structures of Formula AS through the structure of Formula LG1 below:

(LG1)

The isocyanate alkoxysilane may be represented by Formula 1 below:

$$OCN(CH_2)_3SiR_1R_2R_3 \quad \text{[Formula 1]}$$

where at least one of $R_1$ to $R_3$ is an alkoxy group having 1 to 5 carbon atoms, preferably having 1 to 3 carbon atoms, and the remainder are alkyl groups having 1 to 10 carbon atoms.

The alkoxysilylation reaction of the hydroxyl group is performed in the presence of a base catalyst because of the low reactivity of the hydroxyl group in the alkoxysilylation reaction. The examples of the base catalyst, but are not limited to, include amines such as triethylamine, diisopropylethylamine, pyridine, and imidazole. The strong bases such as NaOH or KOH cannot be used because such strong bases opens the epoxide ring and react with isocyanate alkoxysilane to cause side reactions.

These base catalysts may be used alone or in combination of two or more. 0.5 to 1 equivalent of the base catalyst may be used per 1 equivalent of the hydroxyl group of the epoxy compound in consideration of reaction efficiency. If less than 0.5 equivalents of the base catalyst are used, the catalysis efficiency may be insufficient for the reaction. The intended catalysis effect may be obtained by adding 1 equivalent of the base catalyst, and thus an excess thereof is unnecessary.

In the reaction, the epoxy compound having a hydroxyl group reacts with the isocyanate alkoxysilane by the stoichiometric equivalent ratio of the hydroxyl group of the epoxy compound and an alkoxysilane group, and thus 1 equivalent of the hydroxyl group of the epoxy compound is used for the reaction with 1 equivalent of the isocyanate alkoxysilane. Since the hydroxyl group and the alkoxysilane group react with each other by the stoichiometric equivalent ratio thereof, all the hydroxyl groups of the epoxy compound may be alkoxysilylated by reacting 1 equivalent of the isocyanate alkoxysilane with 1 equivalent of the hydroxyl group. Therefore, the hydroxyl group may not remain in the epoxy compound, and an additional process for removing a remaining isocyanate alkoxysilane is not required.

Although the reaction temperature and reaction time of the reaction vary with the reactants, the reaction rate (reactivity) of the hydroxyl group of the epoxy compound is markedly low at a low temperature, and thus a reaction temperature of less than 90° C. may not be preferable. In addition, a reaction temperature of higher than 150° C. may not be preferable, because the thermal stability of the reactants may be decreased during the reaction. Therefore, the reaction may be performed within the temperature range of 90° C. to 150° C.

The reaction may be performed for 72 hours to 120 hours, and preferably for 96 hours to 120 hours. If the reaction time is less than 72 hours, the alkoxysilylation of the hydroxyl group may insufficiently occur, and if the reaction time is greater than 120 hours, it is not preferable because no further reaction occur. Therefore, the reaction may be performed for 72 hours to 120 hours for the alkoxysilylation of the hydroxyl group without insufficient reaction of the hydroxyl group or unnecessary extra reaction time.

In the reaction, a solvent may be arbitrarily used as occasion demands. For example, if the viscosity of the reactants is suitable for reaction at a given reaction temperature, a solvent may not be used. That is, if the viscosity of the reactants is sufficiently low to mix and agitate the reactants, a solvent may not be additionally used. This could be easily determined by a person of ordinary skill in the art. However, if the use of a solvent is needed, any aprotic solvent may be used as long as the aprotic solvent easily dissolves the reactants without any influence on the reaction and the solvent is easily removed after the reaction. Non-limiting examples of the solvent include toluene, acetonitrile, tetrahydrofuran (THF), methyl ethyl ketone (MEK), dimethyl formamide (DMF), dimethyl sulfoxide (DMSO), methylene chloride (MC), or the like. These solvents may be used alone or in combination of two or more.

The amount of the solvent is not particularly limited. For example, a proper amount of the solvent for sufficiently dissolving the reactants without any negative influence on the reaction may be used, and this could be easily determined by a person of ordinary skill in the art.

In the preparation method of an epoxy compound having an alkoxysilyl group according to the present disclosure, an epoxy compound having an alkoxysilyl group is obtained using a hydroxyl group of the epoxy compound without an additional epoxy ring opening reaction.

The method of the present disclosure is simple one-step reaction. In addition, unlike preparation methods of the related art, the epoxide group of a reactant is not consumed. Moreover, an additional reactant is not used for a ring opening reaction and thus, such an additional reactant is not incorporated to the structure of the final epoxy compound, thereby minimizing an EEW increase of the epoxy compound caused by alkoxysilylation. In addition, since a process needed for removing an additional reactant and a strong base used for a ring opening reaction is not required, the overall process may be easily and simply performed. In particular, if a strong base remains, it is inconvenient to remove the strong base used in a first step reaction completely, since a second step reaction of alkoxysilane coupling agent is affected by the residual base.

That is, due to the alkoxysilylation, an EEW increase (ΔEEW, namely, the difference between the EEW of the epoxy compound having the alkoxysilyl group as the product and the EEW of the epoxy compound having the hydroxyl group as the reactant) in the epoxy compound having an alkoxysilyl group prepared by the method of the present disclosure compared to the EEW of the epoxy compound having a hydroxyl group which is a starting material is less than 260/n (where n ranges from 2 to 10 and as described later, refers to the mole ratio of an epoxide group with respect to 1 mol of an alkoxysilyl group in the epoxy compound having an alkoxysilyl group). That is, as compared to the EEW of the epoxy compound having a hydroxyl group which is a starting material, if the EEW of the produced epoxy compound having an alkoxysilyl group is increased by less than 260/n, the epoxy compound having an alkoxysilyl group prepared by the method of the present disclosure has a high concentration of an epoxide group per molecule and thus has good curing characteristics, cross-linking degree, heat resistance, low-temperature curing characteristics, or the like.

Specifically, when the functional group ratio, that is, the mole ratio of [epoxide group]:[alkoxysilyl group] of the produced epoxy compound having a alkoxysilyl group is n:1 (n is a number ranging from 2 to 10), an EEW increase of the produced epoxy compound having an alkoxysilyl group is less than 260/n compared to the EEW of the reactant epoxy compound having a hydroxyl group. For example, if n:1=2:1, the increase in EEW is <130, if n:1=4:1, the increase in EEW is <65, and if n:1=10:1, the increase in EEW is <26.

Since the increase in EEW is minimized as described above, the produced epoxy compound having an alkoxysilyl group has good curing characteristics.

In addition, it is preferable that the mole ratio of [epoxide group]:[alkoxysilyl group] of the produced epoxy compound having a alkoxysilyl group prepared according to the present disclosure is n:1 ranging from 2:1 to 10:1. If the concentration of the alkoxysilyl group increases to the mole ratio of greater than 2:1, it may not be preferable in that the further improvements in physical properties are not obtained by the alkoxysilyl group. If the concentration of the alkoxysilyl group decreases to the mole ratio of below 10:1, the improvements in physical properties by the introduction of the alkoxysilyl group are insufficient and the synthesis of the epoxy compound is practically difficult.

Specifically, the epoxy compound having an alkoxysilyl group prepared by the preparation method of the present disclosure may be represented by Formulae AF to IF below. That is, an epoxy compound having an alkoxysilyl group represented by one of Formulae AF to IF is prepared by the preparation method of the present disclosure.

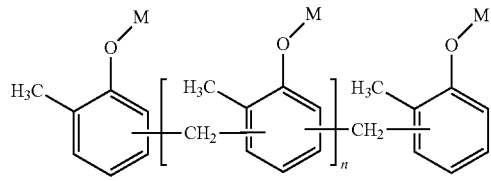

(BF)

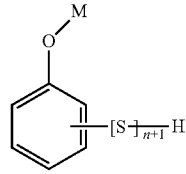

(CF)

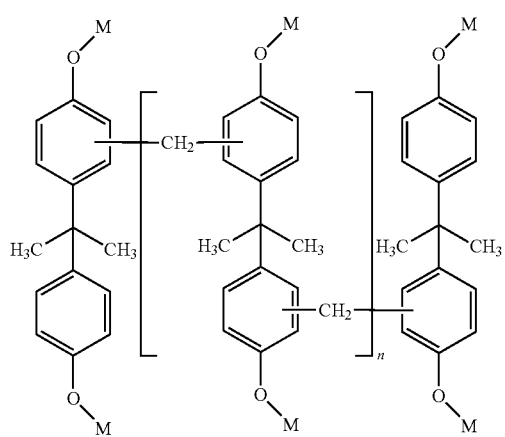

(DF)

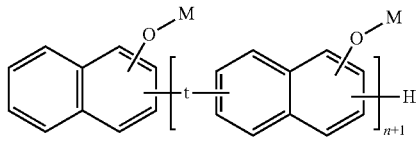

(EF)

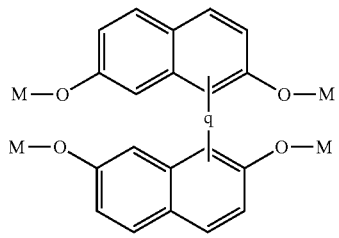

(FF)

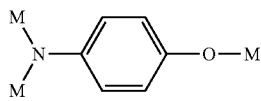

(GF)

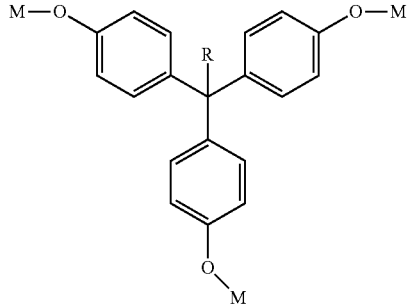

(HF)

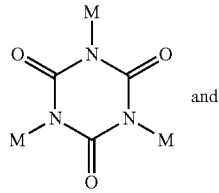

and (IF)

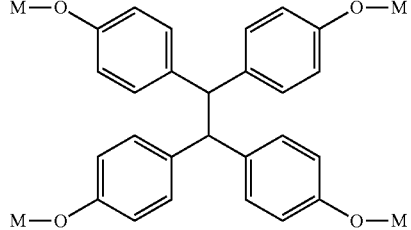

In Formula BF, S is

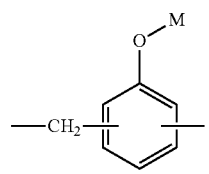

-continued

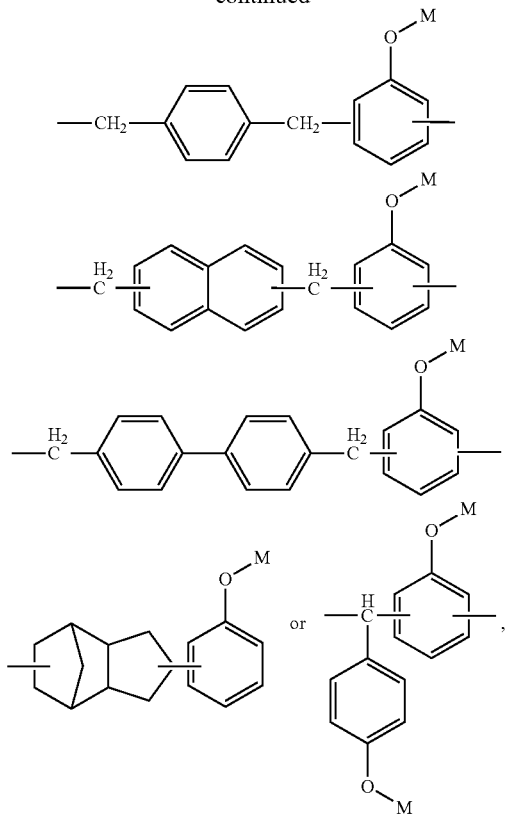

In Formula DF, t is

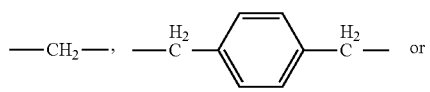

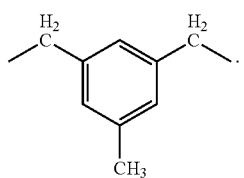

In Formulae AF to DF, n is an integer equal to or greater than 1, preferably within the range of 1 to 30.

In Formula EF, -q- is —CH$_2$— or a direct linkage.

In Formula GF, R is hydrogen, a hydroxyl group, a C1-C10 alkyl group, or a C6 or C10 aromatic group.

In Formulae AF to IF, at least one of Ms is a structure having an alkoxysilyl group selected from the group consisting of —CH$_2$CHOXCH$_2$OX (Formula S21), —CH$_2$CHOXCH$_2$Cl (Formula S22), and —CH(CH$_2$OX)(CH$_2$Cl) (Formula S23), and the remainder are structures having an epoxide group of Formula E1, preferably at least two of the remainder are structures having an epoxide group of Formula E1.

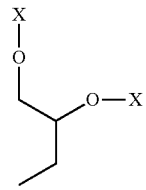

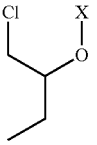

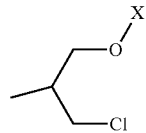

In Formulae S21 to S23, X is CONH(CH$_2$) 3SiR$_1$R$_2$R$_3$, and at least one of R$_1$ to R$_3$ is an alkoxy group having 1 to 5 carbon atoms and the remainder are alkyl groups having 1 to 10 carbon atoms.

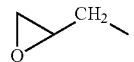

The epoxy compound having an alkoxysilyl group may be in the form of a monomer, an oligomer, or a mixture of a monomer and an oligomer. The term "monomer" refers to a monomer and also to a mixture of identical or different monomers. In addition, the term "oligomer" refers to an oligomer having a combination or mixture of identical or different repeating units.

When two or more structures selected from the group consisting of Formulae AF to IF are connected, the structures may be connected to each other at one of Ms through a linker having an alkoxysilyl group of Formula LG2 below. For example, when two structures of Formula AF are connected to each other, one of Ms of one of the structures of Formula AF is connected to one of Ms of the other of the structures of Formula AF through the structure of Formula LG2 below.

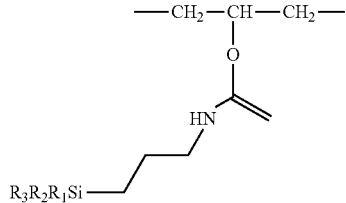

(In Formula LG2, at least one of R$_1$ to R$_3$ is an alkoxy group having 1 to 5 carbon atoms, and the remainder are alkyl groups having 1 to 10 carbon atoms.)

A commercial epoxy compound, specifically an epoxy resin (for example, a commercially available epoxy resin) used as the epoxy compound having a hydroxyl group is in the form of a mixture of an epoxy compound having an epoxide group only and an epoxy compound having an epoxide group and a hydroxyl group produced by side reaction. Therefore, the epoxy compound having an alkoxysilyl group prepared using the epoxy compound having a hydroxyl group may in the form of a mixture of an epoxy compound having an epoxide group only and an epoxy compound having an alkoxysilyl group and an epoxide group.

In the preparation method of an epoxy compound having an alkoxysilyl group of the present disclosure, (1) a hydroxyl group formed by a side reaction is converted into a reactive alkoxysilyl group in the epoxy compound, and (2) the alkoxysilyl group is introduced without loss of an epoxide group which reacts with a curing agent in a curing reaction of the epoxy compound, thereby minimizing an EEW increase of a prepared epoxy compound having an alkoxysilyl group. Therefore, superior physical properties may be obtained upon curing.

The epoxy compound having an alkoxysilyl group prepared by the method of the present disclosure is applicable to any fields, applications and usages to which epoxy compounds of the related art are applicable.

The present disclosure also provides an epoxy composition comprising the epoxy compound having an alkoxysilyl group prepared by the method.

For example, the composition may be used in various applications such as electronic materials, for example, but not limited thereto, semiconductor substrates, for example, IC substrates, laminates in which a metal layer is provided on a base layer of the epoxy composition of the present disclosure, prepreg, encapsulants (packaging materials), printed circuit boards, electronic components, adhesives, paintings, composite materials, or the like. In addition, the composition may be a curable composition and/or curable composition comprising a filler.

It is understood that the composition includes any type and/or combination of epoxy compositions known in the art so long as the composition includes an epoxy compound having an alkoxysilyl group prepared by the method of the present invention. The types and mixing ratio of a curing agent, a curing accelerator (catalyst), a filler (for example, inorganic particles and/or a fiber), a general epoxy compound (epoxy resin), and other additives in the composition are not limited.

The composition may comprise at least one type of epoxy compound having an alkoxysilyl group prepared by the method of the present disclosure. More specifically, the composition may comprise at least one epoxy compound having an alkoxysilyl group selected from the group consisting of Formulae AF to IF. The physical properties of the epoxy composition may be controlled by adjusting the various epoxy compounds in the epoxy composition.

Furthermore, in the technical field of the present disclosure, the epoxy composition, a cured product thereof, and/or a composite thereof may be used together with various types of epoxy compounds (epoxy resins) of the related art to control physical properties for the applications and/or uses.

The epoxy compound of the related art may be, but is not limited to, any epoxy compound (epoxy resin) known in the related art. For example, the epoxy compound of the related art may be at least one selected from the group consisting of a glycidyl ether-based epoxy compound, a glycidyl-based epoxy compound, a glycidyl amine-based epoxy compound, and a glycidyl ester-based epoxy compound. In addition, the epoxy compound of the related art may be at least one selected from the group consisting of a glycidyl ether-based epoxy compound, a glycidyl-based epoxy compound, a glycidyl amine-based epoxy compound, and a glycidyl ester-based epoxy compound which have, as a core structure, a bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, alicyclic, aliphatic, or novolac unit.

For example, but not limited thereto, an epoxy composition according to an aspect of the present disclosure may comprise the epoxy compound of the present disclosure in an amount of 1 wt % to 100 wt % and an epoxy compound of the related art in an amount of 0 wt % to 99 wt % based on the total weight of the epoxy compound; the epoxy compound of the present disclosure in an amount of 10 wt % to 100 wt % and an epoxy compound of the related art in an amount of 0 wt % to 90 wt % based on the total weight of the epoxy compound; the epoxy compound of the present disclosure in an amount of 30 wt % to 100 wt % and an epoxy compound of the related art in an amount of 0 wt % to 70 wt % based on the total weight of the epoxy compound; the epoxy compound of the present disclosure in an amount of 50 wt % to 100 wt % and an epoxy compound of the related art in an amount of 0 wt % to 50 wt % based on the total weight of the epoxy compound; the epoxy compound of the present disclosure in an amount of 10 wt % to less than 100 wt % and an epoxy compound of the related art in an amount greater than 0 wt % to 90 wt %, based on the total weight of the epoxy compound; the epoxy compound of the present disclosure in an amount of 30 wt % to less than 100 wt % and an epoxy compound of the related art in an amount greater than 0 wt % to 70 wt % based on the total weight of the epoxy compound; or the epoxy compound of the present disclosure in an amount of 50 wt % to less than 100 wt % and an epoxy compound of the related art in an amount greater than 0 wt % to 50 wt % based on the total weight of the epoxy compound.

In addition, the epoxy composition may further comprise a filler (for example, inorganic particles and/or a fiber).

The inorganic particles may be any inorganic particles known for improving the physical properties of an epoxy compound of the related art. In a non-limiting example, the inorganic particles may be particles of at least one selected from the group consisting of at least one of metal oxide selected from the group consisting of silica (for example, fused silica and crystalline silica), zirconia, titania, alumina, silicon nitride, and aluminum nitride, and silsesquioxane. The inorganic particles may be used alone or in a mixture of two or more.

If a large amount of silica is used, the fused silica may be used preferably. In this case, fused silica having any of a cataclastic shape and a spherical shape may be used. However, fused silica having a spherical shape may be used preferably to increase the filling factor of the fused silica and suppress an increase in the viscosity of a molten forming material.

The inorganic particles may have a particle size of 0.5 nm to several tens of micrometers (μm) (for example, from 50 μm to 100 μm) may be used for a composite, specifically, for the dispersibility of the inorganic particles or the like. The inorganic particles are dispersed in the epoxy compound, and the dispersibility of the inorganic particles varies with the particle size of the inorganic particles, and thus, it is preferable to use inorganic particles having various particle sizes within the above range. In addition, in order to increase the filling ratio of the inorganic particles, it is preferable to blend the inorganic particles with a wider distribution of particle size.

In the epoxy composition in accordance with an aspect of the present invention, the amount of the inorganic particles in the epoxy compound may be appropriately adjusted in consideration of a decrease in the coefficient of thermal expansion (CTE) of an epoxy composite and appropriate viscosity of the epoxy composition when in use, and use thereof. For example, the amount of the inorganic particles may be 5 wt % to 95 wt %, for example 5 wt % to 90 wt %, for example 10 wt % to 90 wt %, for example 30 wt % to 95 wt %, for example 30 wt % to 90 wt %, for example 5 wt % to 60 wt %, or for example 10 wt % to 50 wt % based on the total weight of the solid content of the epoxy composition (in the case of a cured epoxy product, based on the total weight of the cured epoxy product).

More specifically, in an example, when the epoxy composition is used as a semiconductor encapsulant or the like, the amount of the inorganic particles may be, but are not limited to, within the range of 30 wt % to 95 wt % or, for example, within the range of 30 wt % to 90 wt % based on the total weight of the solid content of the epoxy composition (in the case of a cured epoxy product, based on the total weight of the cured epoxy product) in consideration of the CTE and processability of the semiconductor encapsulant. In another example, when the epoxy composition is used in a semiconductor substrate or the like, the amount of the inorganic particles may be within the range of 5 wt % to 85 wt % or, for example, within the range of 10 wt % to 80 wt % based on the total weight of the solid content of the epoxy composition (in the case of a cured epoxy product, based on the total weight of the cured epoxy product) in consideration of the CTE and strength, or the like of the semiconductor substrate.

Meanwhile, when a fiber is used as a filler, a composite generally may be obtained by impregnating the fiber with the epoxy composition. Thus, the size, or the like of the fiber may not be particularly limited. Any type of fiber commonly used in the technical field of the present disclosure may be used and dimensions thereof may not be limited.

In a non-limiting example, any common fibers used for improving physical properties of cured products of epoxy may be used. Specifically, a glass fiber, an organic fiber, or a mixture thereof may be used. In the present specification, "glass fiber" is a term including a glass fiber fabric, a non-woven glass fiber product, or the like, as well as glass fiber. Non-limiting examples of the glass fiber may include an E-glass fiber, a T-glass fiber, an S-glass fiber, an NE-glass fiber, a D-glass fiber, a quartz glass fiber, or the like. For example, E- or T-glass fiber may be used. The organic fiber may include, but is not limited to, at least one selected from the group consisting of a liquid crystal polyester fiber, a polyethylene terephthalate fiber, a wholly aromatic fiber, a polybenzoxazole fiber, a nylon fiber, a polyethylene naphthalate fiber, a polypropylene fiber, a polyether sulfone fiber, a polyvinylidene fluoride fiber, and a polyether ether ketone fiber. The fibers may be used alone or in combination of two or more.

According to the epoxy composition provided according to one or more of the above-described aspects, the amount of the fiber in the epoxy composition, for example, in a glass fiber composite of the epoxy composition, may be within the range of 10 wt % to 90 wt %, for example within the range of 30 wt % to 70 wt %, or for example within the range of 35 wt % to 70 wt % based on the total weight of a cured product. Thus, the amount of the resin may be within the range of 10 wt % to 90 wt %, for example within the range of 30 wt % to 70 wt %, or for example within the range of 35 wt % to 70 wt %. In the aspect of improvement in heat resistance and processability, the fibers can be blended in the above-mentioned content range. Meanwhile, in an epoxy composition, a cured product, and the like comprising a fiber, the solid portion excluding the fibers in the total solid portion is generally referred to as a resin content (R/C).

Further, according to an aspect, the epoxy composition provided according to one or more of the above-described aspects comprising the fiber may comprise inorganic particles additionally. In this case, the inorganic particles may be comprised in an amount of 1 wt % to 80 wt % based on the total weight of resin amount to improve the physical properties and processability of the epoxy composition. In this case, the kind of the inorganic particles is not specifically limited, and any inorganic particles known in this technical field may be used. For example, the above-described inorganic particles may be used.

The epoxy composition may further comprise a curing agent. The curing agent may be any curing agent commonly known as a curing agent for epoxy compounds. In a non-limiting example, an amine, a polyphenol, an acid anhydride, or the like may be used as the curing agent.

More particularly, examples of the amine curing agent include, but are not limited to, an aliphatic amine, an alicyclic amine, an aromatic amine, other amines and a modified polyamine. In addition, an amine compound including two or more primary amine groups may be used. Specific examples of the amine curing agent may include: at least one aromatic amine selected from the group consisting of 4,4'-dimethylaniline (diamino diphenyl methane, DAM or DDM), diamino diphenyl sulfone (DDS), and m-phenylene diamine; at least one aliphatic amine selected from the group consisting of diethylene triamine (DETA), diethylene tetramine, triethylene tetramine (TETA), m-xylene diamine (MXDA), methane diamine (MDA), N,N'-diethylenediamine (N,N'-DEDA), tetraethylenepentaamine (TEPA), and hexamethylenediamine; at least one alicyclic amine selected from the group consisting of isophorone diamine (IPDI), N-aminoethyl piperazine (AEP), and bis(4-amino 3-methylcyclohexyl)methane (Larominc 260); other amines such as dicyandiamide (DICY); and modified amines such as a polyamide-based amine or an epoxide-based amine.

Examples of the polyphenol curing agent may include, but are not limited to, a phenol novolac resin, a cresol novolac resin, a bisphenol A novolac resin, a xylene novolac resin, a triphenyl novolac resin, a biphenyl novolac resin, a dicyclopentadiene novolac resin, a naphthalene novolac resin, or the like.

Examples of the acid anhydride curing agent may include, but are not limited to, an aliphatic acid anhydrous such as dodecenyl succinic anhydride (DDSA) or poly azelaic poly anhydride; an alicyclic acid anhydride such as hexahydrophthalic anhydride (HHPA), methyl tetrahydrophthalic anhydride (MeTHPA), or methylnadic anhydride (MNA); an aromatic acid anhydride such as trimellitic anhydride (TMA), pyromellitic acid dianhydride (PMDA), or benzophenonetetracarboxylic dianhydride (BTDA); and a halogen-based acid anhydride such as tetrabromophthalic anhydride (TBPA) or chlorendic anhydride.

In general, the crosslinking density of an epoxy composite may be adjusted by the degree of reaction between the curing agent and an epoxide group. According to the range of a target crosslinking density, the amount of the curing agent may be adjusted based on the concentration of the epoxide group of an epoxy compound. For example, in the case in which the amine curing agent is used, the ratio of the epoxy equivalent/amine equivalent may preferably be adjusted to be within the range of 0.5 to 2.0, for example, within the range of 0.8 to 1.5 in reaction between the amine curing agent and the epoxide group.

Although the mixing ratio of the curing agent has been explained with respect to the amine curing agent, a polyphenol curing agent, an acid anhydride curing agent, or any curing agent for curing an epoxy compound not separately illustrated in this specification may also be used by appropriately adding a stoichiometric amount thereof according to a chemical reaction formula of the epoxide functional group and the reactive functional group of the curing agent based on the concentration of the total epoxide group in the epoxy composition according to the range of an intended cross-linking density. This is commonly known in this technical field.

In addition, although an imidazole described below is widely used as a curing accelerator, the imidazole may be used as a single curing agent. In the case in which the imidazole is used as a curing agent, the imidazole may be used in an amount of 0.1 phr to 10 phr (parts per hundred resin: parts by weight based on 100 parts by weight of an epoxy compound) based on the epoxy compound.

Other general additives such as a releasing agent, a surface treatment agent, a flame retardant, a plasticizer, bactericides, a leveling agent, a defoaming agent, a colorant, a stabilizer, a coupling agent, a viscosity controlling agent, a diluent, a rubber, or a thermoplastic resin may be added to the epoxy composition as occasion demands so as to control the physical properties of the epoxy composition within the range of not damaging the physical properties of the epoxy composition.

As described above, the term "epoxy composition" used herein should be understood as comprising the epoxy compound, specifically, an epoxy resin having an alkoxysilyl group according to the present disclosure, and other components added to the epoxy composition as occasion demands such as an optional curing agent, a curing accelerator (catalyst), a filler (for example, inorganic particles and/or a fiber), a common epoxy compound (specifically, an epoxy resin), a solvent, and other additives optionally used in this technical field. Furthermore, in general, the solvent may be optionally used to control the amount of the solid content and/or the viscosity of the epoxy composition in consideration of the processability of the epoxy composition or the like. Meanwhile, the term "total weight of the solid content of the epoxy composition" used in the present disclosure refers to the total weight of the components of the epoxy composition except for the weight of the solvent of the epoxy composition.

Another aspect of the present disclosure provides a cured product comprising, consisting essentially of, or consisting of the epoxy composition provided according to one or more of the above-described aspects of the present disclosure. When the epoxy composition provided according to one or more of the above-described aspects is practically used, for example, when the epoxy composition is used as an electronic material or the like, a cured product of the epoxy composition may be used. In this technical field, a cured product of a composition comprising an epoxy compound and an inorganic filler is generally referred to as a composite.

The epoxy compound provided according to one or more of the above-described aspects of the present disclosure may show good heat resistance in the composite and/or good flame retardancy in the cured product.

Specifically, the composite may have a low CTE, for example, 50 ppm/°C. or less, for example 40 ppm/°C. or less, for example 30 ppm/°C. or less, for example 15 ppm/°C. or less, for example 12 ppm/°C. or less, for example 10 ppm/°C. or less, for example 8 ppm/°C. or less, or for example 6 ppm/°C. or less. The physical properties of the composite improve as the CTE of the composition decreases, and thus the lower limit of the CTE of the composition is not particularly set.

In addition, the glass transition temperature (Tg) of the composite (the cured product comprising a filler) of the present disclosure may be greater than 100° C., for example, equal to or greater than 130° C., or for example, equal to or greater than 250° C. Otherwise, the composite may not have a glass transition temperature (Tg-less). The physical properties of the composite improve as the Tg of the composition increases, and thus the upper limit of the Tg of the composition is not particularly set.

Hereinafter, the preparation method of an epoxy compound having an alkoxysilyl group of the present disclosure will be described in detail through examples.

A. Synthesis Examples

Synthesis Example 1

20 g of cresol novolac epoxy compound (YDCN-500-80P, EEW=220 g/Eq, KuKdo Chemical CO., Ltd., hereinafter referred to as Epoxy 1) as a starting material and 50 ml of toluene were added into a two-neck flask at room temperature and were stirred. Thereafter, 5.62 g of 3-(triethoxysilyl) propyl isocyanate and 2.94 g of diisopropylethylamine (DIPEA) were slowly added to the two-necked flask at room temperature for 10 minutes, followed by heating and stirring at 90° C. for 96 hours. After completion of reaction, the mixture was cooled to room temperature, the solvent and bases (DIPEA) were removed from the mixture, and then the mixture was completely dried using a vacuum pump. Finally, a product, that is, an epoxy compound having an alkoxysilyl group (mole ratio of [epoxide group]:[alkoxysilyl group]=4:1, EEW=282 g/Eq) was synthesized.

NMR of Final Product in Synthesis Example 1

$^1$H NMR (400 MHz, DMSO): δ=7.04-6.62 (m, 76.07H), 4.27-4.16 (m, 9.39H), 4.06-3.37 (m, 152.07H), 3.33-3.07 (m, 28.94H), 3.04-2.91 (m, 13.57H), 2.84-2.52 (m, 50.00H), 2.28-1.96 (m, 96.93H), 1.51-1.36 (m, 15.02H), 1.18-1.07 (m, 68.89H),

TABLE 1

Reaction conditions for synthesis and molecular characteristics of final products

| | | *SE 1 | SE 2 | SE 3 | SE 4 | SE 5 | SE 6 | SE 7 | SE 8 | SE 9 |
|---|---|---|---|---|---|---|---|---|---|---|
| Epoxy compound (g) | Epoxy 1 | 20 | | | | | | | | |
| | Epoxy 2 | | 20 | | | | | | | |

TABLE 1-continued

Reaction conditions for synthesis and molecular characteristics of final products

|  |  | *SE 1 | SE 2 | SE 3 | SE 4 | SE 5 | SE 6 | SE 7 | SE 8 | SE 9 |
|---|---|---|---|---|---|---|---|---|---|---|
| Epoxy 3 |  |  |  | 20 |  |  |  |  |  |  |
| Epoxy 4 |  |  |  |  | 20 |  |  |  |  |  |
| Epoxy 5 |  |  |  |  |  | 20 |  |  |  |  |
| Epoxy 6 |  |  |  |  |  |  | 20 |  |  |  |
| Epoxy 7 |  |  |  |  |  |  |  | 20 |  |  |
| Epoxy 8 |  |  |  |  |  |  |  |  | 20 |  |
| Epoxy 9 |  |  |  |  |  |  |  |  |  | 20 |
| 3-(triethoxysilyl)propyl isocyanate (g) |  | 5.62 | 4.56 | 5.89 | 4.67 | 7.63 | 12.37 | 7.73 | 11.79 | 5.89 |
| DIPEA (g) |  | 2.94 | 2.38 |  |  |  |  |  |  |  |
| Triethylamine (g) |  |  |  | 2.41 | 1.91 | 3.12 | 5.06 | 3.16 | 4.82 | 2.41 |
| Toluene (ml) |  | 50 | 50 | 50 | 50 | 50 | 50 | 50 | 50 | 50 |
| Synthesis conditions (reaction time/temperature) |  | 96 h/ 90° C. | 96 h/ 90° C. | 96 h/ 120° C. | 96 h/ 120° C. | 120 h/ 90° C. | 120 h/ 90° C. | 120 h/ 90° C. | 120 h/ 90° C. | 120 h/ 90° C. |
| EEW of starting material (g/Eq) |  | 220 | 271 | 210 | 265 | 162 | 100 | 160 | 105 | 210 |
| molecular characteristic of final product | mole ratio of [epoxide group]:[alkoxysilyl group] | 4:1 | 4:1 | 4:1 | 5:1 | 5:1 | 6.7:1 | 6.7:1 | 10:1 | 3.3:1 |
|  | EEW (g/Eq) | 282 | 330 | 272 | 315 | 212 | 137 | 197 | 130 | 284 |

*SE: Synthesis Example

Synthesis Example 2

A silylated biphenyl novolac epoxy compound was synthesized using a biphenyl novolac epoxy compound (NC3000L, Nippon Kayaku Co., Ltd. EEW=271 g/Eq, hereinafter referred to as Epoxy 2). Reactants and reaction conditions shown in Table 1 were used, and after a reaction proceeded as described in Synthesis Example 1, a final product was obtained.

NMR of Final Product in Synthesis Example 2

$^1$H NMR (400 MHz, DMSO): δ=7.53-6.87 (m, 92.67H), 4.31-4.22 (m, 10.07H), 4.03-3.72 (m, 24.08H), 3.37-3.27 (m, 13.54H), 3.00-2.90 (m, 5.08H), 2.83-2.78 (m, 9.84H), 2.70-2.66 (m, 10.00H), 1.56-1.38 (m, 5.19H), 1.17-1.12 (m, 27.25H), 0.57-0.50 (m, 5.07H)

Synthesis Example 3

A silylated bisphenol A novolac epoxy compound was synthesized using a bisphenol A novolac epoxy compound (HiROXY® KEB-3180, Kolon Industries, Inc. EEW=210 g/Eq, hereinafter referred to as Epoxy 3). Reactants and reaction conditions shown in Table 1 were used, and after a reaction proceeded as described in Synthesis Example 1, a final product was obtained.

NMR of Final Product in Synthesis Example 3

$^1$H NMR (400 MHz, DMSO): δ=7.12-6.58 (m, 20.70H), 4.33-4.01 (m, 5.89H), 3.86-3.58 (m, 17.34H), 3.32-3.03 (m, 5.61H), 3.01-2.90 (m, 4.02H), 2.85-2.53 (m, 10.00H), 1.56-1.26 (m, 17.49H), 1.19-1.01 (m, 14.44H), 0.59-0.46 (m, 2.66H)

Synthesis Example 4

A silylated naphthalene novolac epoxy compound was synthesized using a naphthalene novolac epoxy compound (ESN-175, Nippon Steel & Sumikin Chemical Co., Ltd. EEW=265 g/Eq, hereinafter referred to as Epoxy 4). Reactants and reaction conditions shown in Table 1 were used, and after a reaction proceeded as described in Synthesis Example 1, a final product was obtained.

NMR of Final Product in Synthesis Example 4

$^1$H NMR (400 MHz, DMSO): δ=8.04-8.02 (m, 2.07H), 7.89-7.52 (m, 9.81H), 7.39-7.01 (m, 11.43H), 6.59-6.52 (m, 4.52H), 4.52-4.46 (m, 13.65H), 4.42-3.60 (m, 23.46H), 3.33-3.28 (m, 6.33H), 2.98-2.90 (m, 2.64H), 2.75-2.59 (m, 14.01H), 1.56-1.39 (m, 2.71H), 1.20-1.11 (m, 13.43H), 0.57-0.49 (m, 2.66H)

Synthesis Example 5

A silylated binaphthalene epoxy compound was synthesized using tetraglycidyl ether of bisnaphthalene (EEW=162 g/Eq, hereinafter referred to as Epoxy 5). Reactants and reaction conditions shown in Table 1 were used, and after a reaction proceeded as described in Synthesis Example 1, a final product was obtained.

NMR of Final Product in Synthesis Example 5

$^1$H NMR (400 MHz, DMSO): δ=7.88-6.84 (m, 13.42H), 4.84 (s, 1.92H), 4.57-3.91 (m, 11.09H), 3.31-3.15 (m, 4.54H), 2.99-2.54 (m, 12.57H), 1.57-1.37 (m, 2.10H), 1.17-1.11 (m, 9.89H), 0.56-0.51 (m, 2.03H)

Synthesis Example 6

A silylated aminophenol epoxy compound was synthesized using an aminophenol epoxy compound (Araldite® MY0510, Huntsman CO., Ltd. EEW=100 g/Eq, hereinafter referred to as Epoxy 6). Reactants and reaction conditions shown in Table 1 were used, and after a reaction proceeded as described in Synthesis Example 1, a final product was obtained.

NMR of Final Product in Synthesis Example 6

$^1$H NMR (400 MHz, DMSO): δ=6.90-6.72 (m 4H), 5.28-5.26 (m, 0.37H), 4.22-4.10 (m, 1.69H), 3.80-3.54 (m, 7.13H), 3.36-3.25 (m, 3.85H), 3.11-3.06 (m, 1.76H), 3.01-

2.90 (m, 0.79H), 2.83-2.80 (m, 1.32H), 2.74-2.71 (m, 2.64H), 2.68-2.66 (m, 1.33H), 2.57-2.54 (m, 2.64H), 1.56-1.38 (m, 0.79H), 1.17-1.12 (m, 3.68H), 0.55-0.50 (m, 0.77H)

Synthesis Example 7

A silylated triphenylmethane epoxy compound was synthesized using a triphenylmethane epoxy compound (Tactix® 742, Huntsman CO., Ltd. EEW=160 g/Eq, hereinafter referred to as Epoxy 7). Reactants and reaction conditions shown in Table 1 were used, and after a reaction proceeded as described in Synthesis Example 1, a final product was obtained.

NMR of Final Product in Synthesis Example 7

$^1$H NMR (400 MHz, DMSO): δ=7.03-6.73 (m, 12H), 5.79-5.78 (m, 0.41H), 5.38 (s, 0.99H), 4.50-4.13 (m, 3.22H), 3.82-3.61 (m, 6.01H), 3.40-3.30 (m, 2.65H), 3.00-2.91 (m, 0.87H), 2.92-2.87 (m, 2.70H), 2.76-2.73 (m, 2.69H), 1.57-1.38 (m, 0.79H), 1.17-1.12 (m, 3.99H), 0.56-0.48 (m, 0.78H)

Synthesis Example 8

A silylated triglycidyl isocyanate epoxy compound was synthesized using a triglycidyl isocyanate compound (EEW=105 g/Eq, hereinafter referred to as Epoxy 8). Reactants and reaction conditions shown in Table 1 were used, and after a reaction proceeded as described in Synthesis Example 1, a final product was obtained.

NMR of Final Product in Synthesis Example 8

$^1$H NMR (400 MHz, DMSO): δ=5.31-5.29 (m, 0.24H), 4.06-3.85 (m, 3.28H), 3.78-3.61 (m, 2.08H), 3.17-3.15 (m, 2.76H), 3.01-2.90 (m, 0.51H), 2.76-2.73 (m, 2.72H), 2.62-2.58 (m, 2.73H), 1.56-1.37 (m, 0.52H), 1.17-1.12 (m, 2.32H), 0.56-0.49 (m, 0.52H)

Synthesis Example 9

A silylated tetraphenylethane epoxy compound was synthesized using a tetraphenylethane epoxy compound (Hi-ROXY® KET-4131, Kolon Industries, Inc, EEW=105 g/Eq, hereinafter referred to as Epoxy 9). Reactants and reaction conditions shown in Table 1 were used, and after a reaction proceeded as described in Synthesis Example 1, a final product was obtained.

NMR of Final Product in Synthesis Example 9

$^1$H NMR (400 MHz, DMSO): δ=7.58-6.54 (m, 23.25H), 4.50-4.02 (m, 5.66H), 3.99-3.55 (m, 13.00H), 3.34-3.20 (m, 3.39H), 2.99-2.58 (m, 11.33H), 1.56-1.37 (m, 2.38H), 1.16-1.06 (m, 12.23H), 0.61-0.45 (m, 2.26H)

B. Comparative Synthesis Examples

Comparative Synthesis Example 1

In Comparative Synthesis Examples 1-1 to 1-3, epoxy compounds having an alkoxysilyl group were synthesized under the same conditions as those in Synthesis Example 1 except for the optional use of diisopropylethylamine (DIPEA) as a base and reaction conditions (temperature/time) shown in Table 2 below.

TABLE 2

| | Use of base (diisopropyl-ethylamine) | Reaction temperature | Reaction time | Remaining of unreacted 3-(triethoxysilyl) propyl isocyanate (Alpha-H peak @ 0.7 ppm) |
|---|---|---|---|---|
| Synthesis Example 1 | ○ | 90° C. | 96 hours | X |
| Comparative Synthesis Example 1-1 | X | 90° C. | 96 hours | ○ |
| Comparative Synthesis Example 1-2 | ○ | 65° C. | 30 hours | ○ |
| Comparative Synthesis Example 1-3 | ○ | 90° C. | 48 hours | ○ |

In Synthesis Example 1, unreacted 3-(triethoxysilyl)propyl isocyanate was not observed. Unlike in Synthesis Example 1, when synthesis reaction proceeded without the use of a base or under reaction conditions (temperature/time) outside the ranges proposed in the present disclosure, alkoxysilylation was not completed, and thus unreacted 3-(triethoxysilyl)propyl isocyanate was observed in an NMR spectrum.

Comparative Synthesis Example 2: Preparation of Epoxy Compound Having Alkoxysilyl Group Using Epoxy Ring-Opening Reaction Epoxy 1 (25 g), NaOH (0.83 g), tetraethylammonium bromide (NEt$_4$Br, 1.01 g), tetrahydrofuran (THF, 50 ml), CH$_3$CN (50 ml), and ethanol (EtOH, 68 ml) were added into a two-neck flask at room temperature and were stirred at 26° C. for 4 hours. Thereafter, 5 ml of a saturated solution of ammonium chloride (NH$_4$Cl) was added to the mixture, and the mixture was stirred for 3 minutes. Then, the solvent was removed using a rotary evaporator, and workup was performed using 400 ml of ethyl acetate (EA) and 300 ml of water to separate an organic layer. MgSO$_4$ was added to the separated organic layer to remove the residual H$_2$O. A ring-opened epoxy intermediate was obtained, followed by filtering and evaporating of the solvent.

Thereafter, 20 g of the intermediate obtained above, 26.0 ml of 3-(triethoxysilyl)propyl isocyanate, 18.1 ml of N,N-diisopropylethylamine (DIPEA), and 130 ml of CH$_3$CN were added into a two-neck flask and were stirred at 65° C. for 20 hours. After completion of reaction, 300 ml of ethyl acetate was added to the mixture, and the mixture was worked up using a saturated aqueous solution of ammonium chloride (NH$_4$Cl). An organic layer was separated, and MgSO$_4$ was added to the organic layer to remove the residual H$_2$O. Hexane was added to the crude product from which an organic solvent had been removed using an evaporator, and the product was kept at −15° C. for precipitation. After removing a supernatant, a process of adding hexane to a precipitate for precipitation was repeated twice. An epoxy compound having a mole ratio of [epoxide group]:[alkoxysilyl group] of 4:1 was obtained.

Comparative Synthesis Examples 3 to 5

In Comparative Synthesis Examples 3 to 5, epoxy compounds having an alkoxysilyl group were prepared by ring opening reaction as described in Comparative Synthesis Example 2 except that Epoxy 2 to 4 were used as starting materials.

Comparison of EENs of Alkoxysilyl Epoxy Compounds (Present Disclosure VS Preparation Method Using the Epoxy Ring-Opening Reaction)

EEW values of the epoxy compounds having an alkoxysilyl group of Synthesis Examples 1 to 4 were compared with those of the epoxy compounds having an alkoxysilyl group prepared in Comparative Synthesis Examples 2 to 5 by ring-opening reaction (Korean Patent Application No. 10-2014-0021884, ring-opening reaction using EtOH), wherein all the epoxy compound have the same alkoxysilyl group concentration, and are shown in Table 3 below.

TABLE 3

| | | Epoxy compound having an alkoxysilyl group | |
|---|---|---|---|
| | | EEW (g/Eq) | |
| starting material | mole ratio of [epoxide group]:[alkoxysilyl group] | Examples of the present invention | Ring-opening reaction method (KR 10-2014-0021884) |
| Epoxy 1 | 4:1 | 282 (Synthesis Example 1) | 348 (Comparative Synthesis Example 2) |
| Epoxy 2 | 4:1 | 330 (Synthesis Example 2) | 412 (Comparative Synthesis Example 3) |
| Epoxy 3 | 4:1 | 272 (Synthesis Example 3) | 336 (Comparative Synthesis Example 4) |
| Epoxy 4 | 5:1 | 315 (Synthesis Example 4) | 377 (Comparative Synthesis Example 5) |

As shown in Table 3 above, EEW values of Synthesis Examples 1 to 4 and Comparative Synthesis Examples 2 to 5 were compared under the same condition of the mole ratio of [epoxide group]:[alkoxysilyl group]. The EEW values of the epoxy compounds having an alkoxysilyl group prepared in Synthesis Examples 1 to 4 by the present disclosure were markedly lower than the EEW values of the epoxy compounds having an alkoxysilyl group prepared in Comparative Synthesis Examples 2 to 5. Therefore, it can be understood that the epoxy compounds having an alkoxysilyl group prepared by the method of the present disclosure has a high concentration of an epoxide group per molecule and thus has good curing characteristics.

C. Physical Property Evaluation: Preparation of Cured Product and Heat Resistance Evaluation (1) Preparation of Epoxy Filler Composites (Cured Products)

An epoxy compound, silica, and wax were dissolved in methyl ethyl ketone according to the formulation described in Table 4 below to have a solid content of this solution of 70 wt %. This mixture solution was stirred for 20 minutes, and after adding a curing agent thereto, the mixture solution was further stirred for 10 minutes. Then, a catalyst was added to the mixture solution, and the mixture solution was further stirred for 10 minutes to make the homogeneous solution. Then, the mixture solution was placed in a convection oven heated to 80'C to remove the solvent, and was cured at 180° C. for 4 hours by using a preheated hot press. In this manner, epoxy filler (inorganic particles) composites (5 mm×5 mm×3 mm) were obtained. In the meantime, after the curing at 180° C., a sample of Comparative Property Example 3 was further cured at 230° C. for 2 hours to observe high-temperature curing effects.

(2) Heat Resistance Evaluation

Dimensional changes of cured products which have the formulations as shown in Table 4 below were evaluated as a function of the temperature by using a thermo-mechanical analyzer, and results thereof are shown in Table 4 below. Epoxy filler composite samples had a size of 5×5×3 ($mm^3$).

TABLE 4

| | | \*\* PE 1 | PE 2 | PE 3 | PE 4 | PE 5 | PE 6 | PE 7 | PE 8 | PE 9 | \*\*\* CPE 1 | CPE 2 | CPE 3 |
|---|---|---|---|---|---|---|---|---|---|---|---|---|---|
| Epoxy compound of the present invention (g) | \* SE 1 | 3 | | | | | | | | | | | |
| | SE 2 | | 3 | | | | | | | | | | |
| | SE 3 | | | 3 | | | | | | | | | | |
| | SE 4 | | | | 3 | | | | | | | | |
| | SE 5 | | | | | 3 | | | | | | | |
| | SE 6 | | | | | | 3 | | | | | | |
| | SE 7 | | | | | | | 3 | | | | | |
| | SE 8 | | | | | | | | 3 | | | | |
| | SE 9 | | | | | | | | | 3 | | | |
| YDCN-500-80P[(1)] (g) | | | | | | | | | | | 3 | | |
| Comparative Synthesis Example 2 (g) | | | | | | | | | | | | 3 | 3 |
| HF-1M[(2)] (g) | | 1.37 | 1.17 | 1.42 | 1.22 | 1.82 | 2.81 | 1.96 | 2.96 | 1.36 | 1.61 | 1.13 | 1.13 |
| 2P4MHZ[(3)] (g) | | 0.21 | 0.21 | 0.21 | 0.21 | 0.21 | 0.21 | 0.21 | 0.21 | 0.21 | 0.21 | 0.21 | 0.21 |
| WAX-E[(4)] (g) | | 0.01 | 0.01 | 0.01 | 0.01 | 0.01 | 0.01 | 0.01 | 0.01 | 0.01 | 0.01 | 0.01 | 0.01 |
| Silica (g) | | 26.01 | 24.88 | 26.29 | 25.16 | 28.67 | 30.15 | 29.35 | 35.02 | 25.95 | 27.37 | 24.65 | 24.65 |
| Final curing temperature | | | | | | | 180° C. | | | | | | 230° C. |
| CTE (ppm/° C.) | @ 60-100° C. | 8.6 | 10.7 | 9.9 | 10.8 | 10.1 | 10.9 | 10.8 | 11.1 | 10.2 | 12.1 | 15.6 | 9.7 |
| | @ 200-250° C. | 14.2 | 25.4 | 21.8 | 23.7 | 22.6 | 23.8 | 19.5 | 26.9 | 20.3 | 45.6 | 27.3 | 16.7 |

\* SE: Synthesis Example,
\*\* PE: Property Example,
\*\*\* CPE: Comparative Property Example Note) The compounds in Table 4 above are as follows.

(1) Cresol novolac epoxy compound (YDCN-500-80P, EEW=220 g/Eq, KuKdo Chemical CO., Ltd)

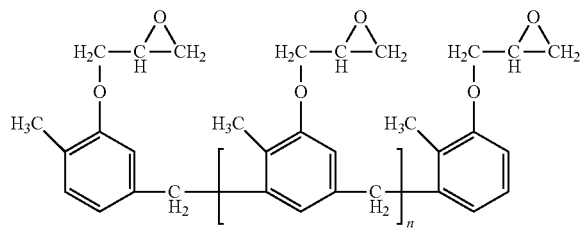

(2) HF-1M: phenol novolac-based curing agent (Meiwa Plastic Industries, HEW-107)

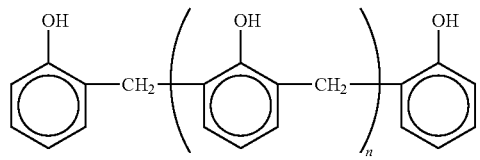

(3) 2P4MHZ: imidazole-based catalyst (Curezol. Shikoku)

(4) WAX-E: Licowax E (Clariant)

As shown in Table 4, composites prepared using the epoxy compounds having an alkoxysilyl group of Synthesis Examples 1 to 9 according to the present disclosure had good CTE characteristics. The performance of the present disclosure was compared with thermal expansion property of a composite prepared using a commercial epoxy compound not having an alkoxysilyl group (Comparative Property Example 1) and a composite prepared using an epoxy compound having an alkoxysilyl group obtained through a ring-opening reaction as disclosed in a patent application (Comparative Property Example 2). Results thereof are shown in FIGURE.

As shown in FIGURE, the CTE of the epoxy compound having an alkoxysilyl group of the present disclosure was lower than the CTE of the commercial epoxy compound (epoxy resin). Therefore, the epoxy compound of the present disclosure had high heat resistance owing to alkoxysilylation. In addition, when the curing temperature was lower to 180° C., the CTE of the epoxy compound having an alkoxysilyl group of the present disclosure was improved compared to the epoxy compound having an alkoxysilyl group synthesized by the ring opening reaction method in Comparative Synthesis Example 2. The epoxy compound having an alkoxysilyl group prepared in Comparative Synthesis Example 2 required additional curing at 230° C. to have physical properties similar to those of the epoxy compound of the present disclosure (Synthesis Example 1). Based on the above, it may be understood that an EEW increase of the epoxy compound having an alkoxysilyl group prepared by the method of the present disclosure is minimized, and thus good curing characteristics, that is, high heat resistance at a low curing temperature, may be obtained.

That is, an EEW increase of the epoxy compound having an alkoxysilyl group prepared by the method of the present disclosure is minimized, and thus the epoxy compound having an alkoxysilyl group of the present disclosure has an improved curing rate compared to epoxy compounds having an alkoxysilyl group prepared through a ring-opening reaction in the related art. Therefore, the epoxy compound of the present disclosure may be efficiently cured at a low curing temperature compared to epoxy compounds having an alkoxysilyl group prepared through a ring opening reaction in the related art.

According to the method of the present disclosure, an epoxy compound having an alkoxysilyl group is prepared by introducing an alkoxysilyl group to a hydroxyl group which most commercial epoxy compounds have. In addition, according to the preparation method of an epoxy compound having an alkoxysilyl group of the present disclosure, an alkoxysilyl group which is a reactive functional group is added to a hydroxyl group which is a defective structure formed during the synthesis of epoxy, thereby improving the physical properties of the epoxy compound. In addition, the preparation method of an epoxy compound having an alkoxysilyl group of the present disclosure is a one-step reaction method, which is simpler than preparation methods proposed by the present applicant (Korean Patent Application Nos. 10-2013-0111473 and 10-2014-0021884). Furthermore, unlike the related art, an increase in EEW is minimized because an epoxide group of a starting material is not consumed and additional reactants such as a ring opening agent are not incorporated. In addition, unlike the related art, it is not necessary to carefully remove strong bases and reactants (for example, a ring opening agent) used in each reaction step so that they are not remain in a final product, and thus overall reaction processes may be performed easily and simply.

In addition, when the epoxy compound having an alkoxysilyl group prepared by the method of the present disclosure is cured, the alkoxysilyl group participates in the epoxy curing reaction (a reaction between an epoxide group of the epoxy compound and a functional group of a curing agent) and an interfacial reaction with a filler. Moreover, the epoxy compound has good physical properties because an EEW increase of the epoxy compound is minimized, and thus a cured product and/or a composite comprising the epoxy compound may have good curing characteristics.

An EEW increase of the epoxy compound having an alkoxysilyl group prepared by the method of the present disclosure is minimized, and the epoxy compound has an appropriate ratio of an epoxide group and the alkoxysilyl group. Therefore, a cured product and/or a composite comprising the epoxy compound have high heat resistance, that is, a low CTE.

In addition, since an EEW increase of the epoxy compound having an alkoxysilyl group prepared by the method of the present disclosure is minimized, the curing rate of the epoxy compound is improved compared to the curing rate of epoxy compounds having an alkoxysilyl group prepared through a ring opening reaction in the related art. Therefore, the epoxy compound of the present disclosure may be cured at a lower curing temperature efficiently and easily, compared to epoxy compounds having an alkoxysilyl group prepared through a ring opening reaction in the related art.

While exemplary embodiments have been shown and described above, it will be apparent to those skilled in the art that modifications and variations could be made without departing from the scope of the present invention as defined by the appended claims.

What is claimed is:

1. A method of preparing an epoxy compound having an alkoxysilyl group, the method comprising reacting an epoxy compound having a hydroxyl group as a starting material with an isocyanate alkoxysilane of Formula 1 in the presence of at least one amine-based base catalyst selected from the group consisting of triethylamine, diisopropylethylamine, pyridine, and imidazole,
- wherein the hydroxyl group of the epoxy compound having a hydroxyl group as a starting material is formed by a side reaction during a synthesis of the epoxy compound,
- wherein 0.5 to 1 equivalent of the amine-based catalyst is used per 1 equivalent of the hydroxyl group of the epoxy compound having a hydroxyl group as a starting material,
- wherein the epoxy compound having an alkoxysilyl group has a mole ratio of [epoxide group]:[alkoxysilyl group] of n:1 ranging from 2:1 to 10:1, and
- an increase in an epoxy equivalent weight (EEW) of the epoxy compound having an alkoxysilyl group is less than 260/n (where n is mole ratio of an epoxide group to 1 mol of the alkoxysilyl group in the epoxy compound having an alkoxysilyl group, and n ranges from 2 to 10) compared to an EEW of the epoxy compound having a hydroxyl group as a starting material, $$OCN(CH_2)_3SiR_1R_2R_3 \quad \text{Formula 1}$$

where at least one of $R_1$ to $R_3$ is an alkoxy group having 1 to 5 carbon atoms, and the remainder are alkyl groups having 1 to 10 carbon atoms.

2. The method of claim 1, wherein the epoxy compound having a hydroxyl group as a starting material is selected from the group consisting of Formulae AS to IS below:

(AS)

(BS)
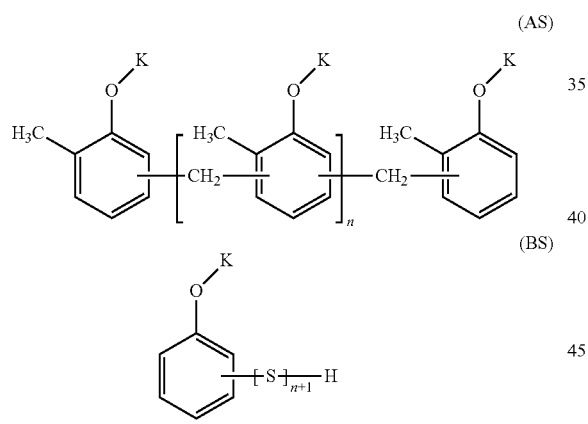

(CS)
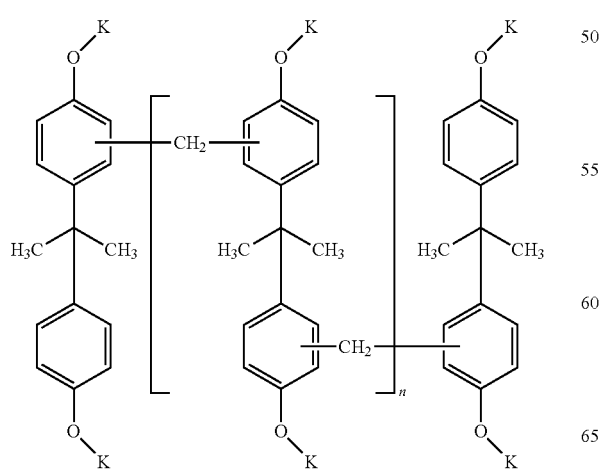

(DS)
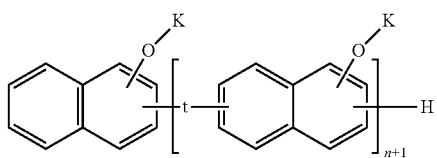

(ES)
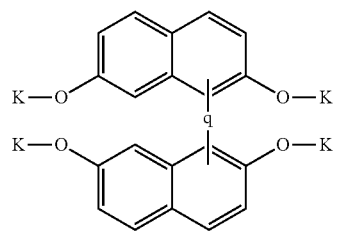

(FS)
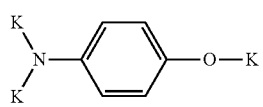

(GS)
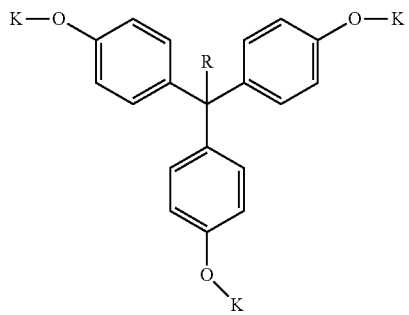

(HS)
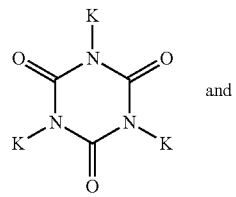

and (IS)
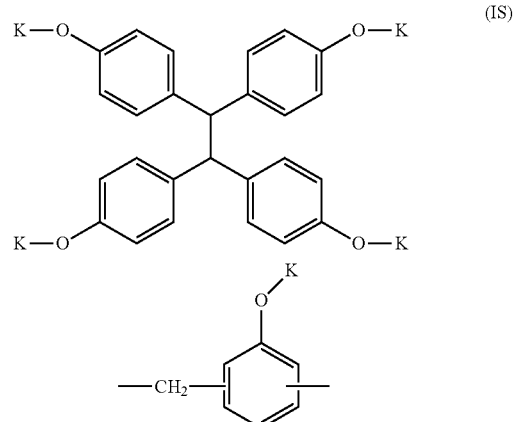

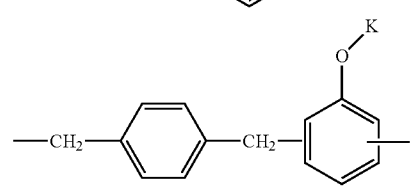

-continued

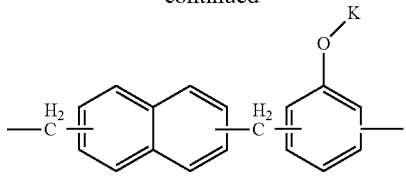

in Formula BS, S is

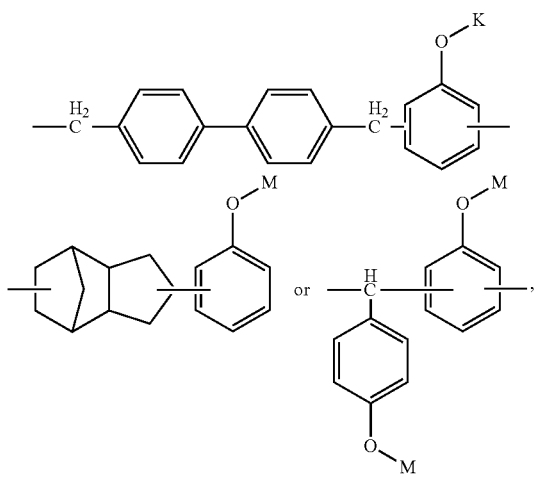

in Formula DS, t is

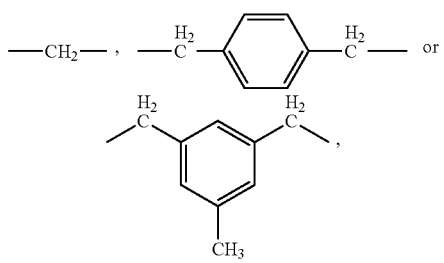

in Formulae AS to DS, n is an integer equal to or greater than 1,
in Formula ES, -q- is —CH$_2$— or a direct linkage,
in Formula GS, R is hydrogen, a hydroxyl group, a C1-C10 alkyl group, or a C6 or C10 aromatic group,
in Formulae AS to IS, at least one of Ks is a structure having a hydroxyl group selected from the group consisting of —CH$_2$CHOHCH$_2$OH (Formula S11), —CH$_2$CHOHCH$_2$Cl (Formula S12), and —CH(CH$_2$OH)(CH$_2$Cl) (Formula S13), and the remainder are structures having an epoxide group of Formula E1 below:

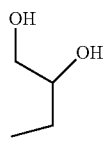
(S11)

-continued

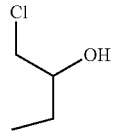
(S12)

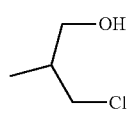
(S13)

(E1)

wherein the structures of Formulae AS to IS may be connected through a linker having a hydroxyl group of Formula LG1 below at one position of Ks:

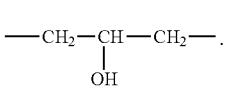
(LG1)

3. The method of claim 1, wherein 1 equivalent of the hydroxyl group of the epoxy compound having a hydroxyl as a starting material group reacts with 1 equivalent of the isocyanate alkoxysilane of Formula 1.

4. The method of claim 1, wherein the reacting is performed at a temperature range of 90° C. to 150° C.

5. The method of claim 1, wherein the reacting is performed for 72 hours to 120 hours.

6. The method of claim 1, wherein the epoxy compound having an alkoxysilyl group is one-selected from the group consisting of Formulae AF to IF below:

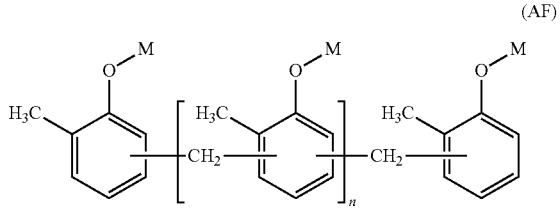
(AF)

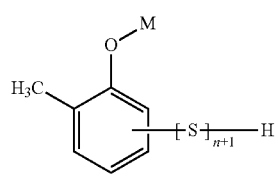
(BF)

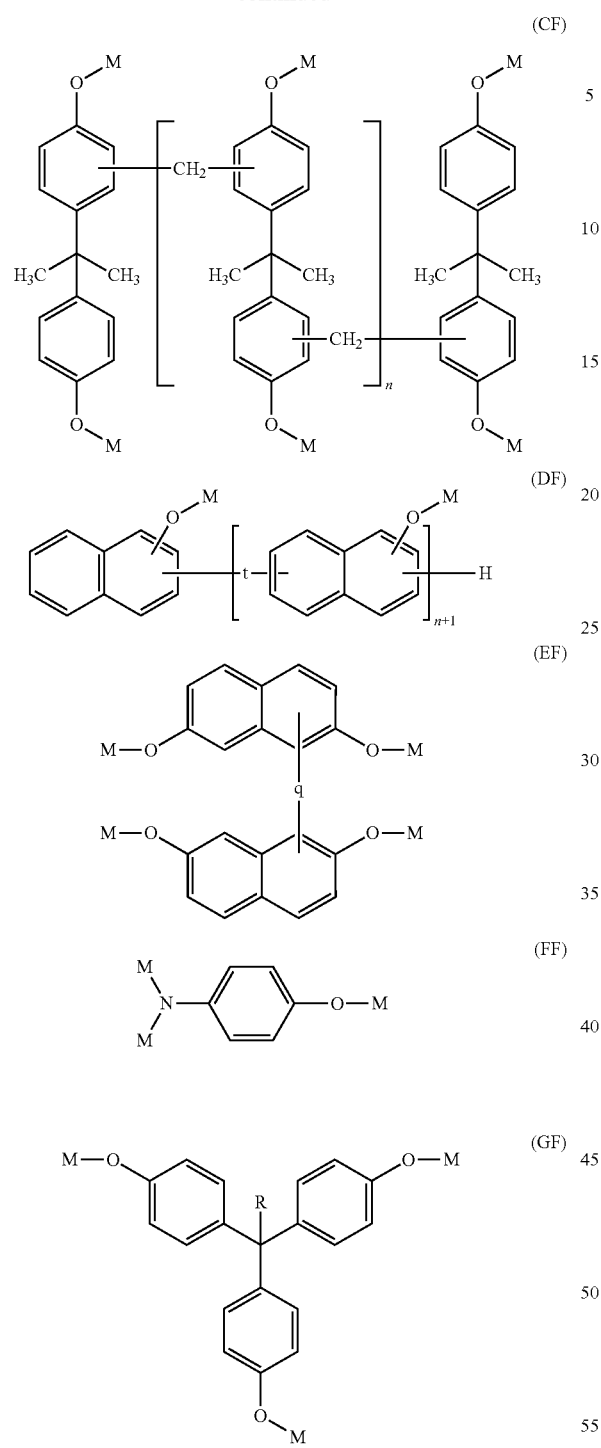
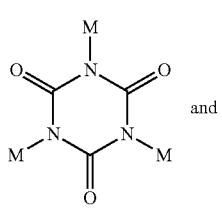
in Formula BF, S is
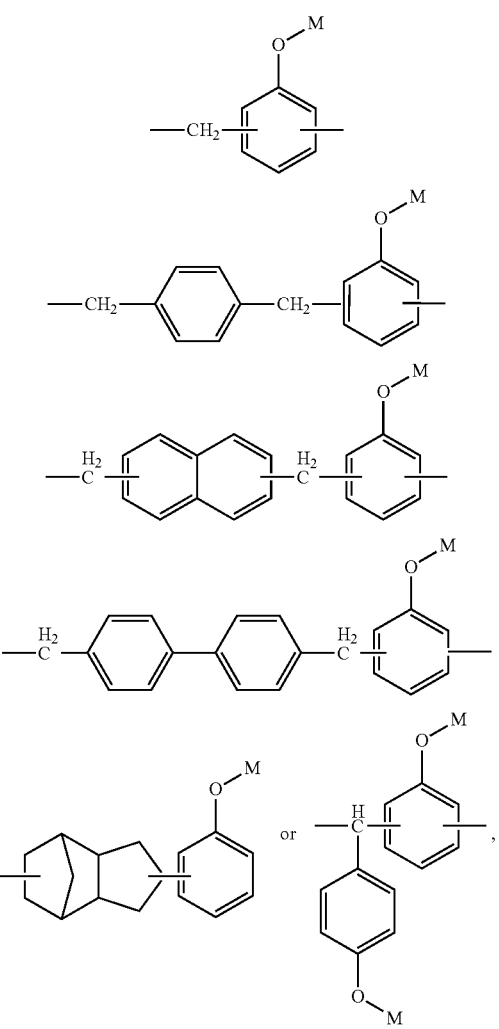
in Formula DF, t is
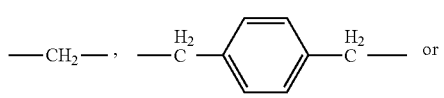

-continued

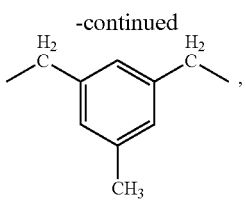

in Formulae AF to DF, n is an integer equal to or greater than 1,
in Formula EF, -q- is —CH$_2$— or a direct linkage,
in Formula GF, R is hydrogen, a hydroxyl group, a C1-C10 alkyl group, or a C6 or C10 aromatic group,
in Formulae AF to IF, at least one of Ms is a structure having an alkoxysilyl group selected from the group consisting of —CH$_2$CHOXCH$_2$OX (Formula S21), —CH$_2$CHOXCH$_2$Cl (Formula S22), and —CH(CH$_2$OX)(CH$_2$Cl) (Formula S23), and the remainder are structures having an epoxide group of Formula E1 below:

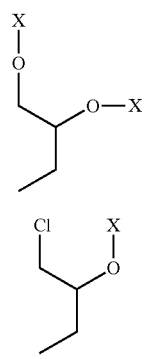

-continued

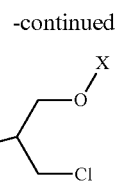 (S23)

in Formulae S21 to S23, X is CONH(CH$_2$)$_3$SiR$_1$R$_2$R$_3$, wherein at least one of R$_1$ to R$_3$ is an alkoxy group having 1 to 5 carbon atoms and the remainder are alkyl groups having 1 to 10 carbon atoms,

 (E1)

wherein the structures of Formulae AF to IF may be connected to each other at one of Ms through a linker having an alkoxysilyl group of Formula LG2 below:

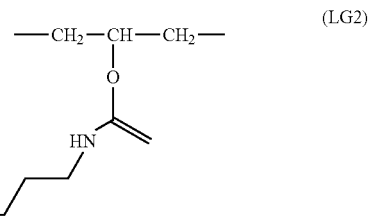 (LG2)

in Formula LG2, at least one of R$_1$ to R$_3$ is an alkoxy group having 1 to 5 carbon atoms, and the remainder are alkyl groups having 1 to 10 carbon atoms.

* * * * *